(12) United States Patent
Kim et al.

(10) Patent No.: US 11,248,024 B2
(45) Date of Patent: Feb. 15, 2022

(54) NOXA-DERIVED, CELL DEATH-INDUCING PEPTIDE EMTD

(71) Applicant: INDUSTRY-ACADEMIC COOPERATION FOUNDATION, CHOSUN UNIVERSITY, Gwangju (KR)

(72) Inventors: Tae-Hyoung Kim, Gwangju (KR); Junghee Park, Gwangju (KR); Ji-Hye Han, Gwangju (KR); Seung-Hyun Myung, Gwangju (KR)

(73) Assignee: INDUSTRY-ACADEMIC COOPERATION FOUNDATION, CHOSUN UNIVERSITY, Gwangju (KR)

( * ) Notice: Subject to any disclaimer, the term of this patent is extended or adjusted under 35 U.S.C. 154(b) by 0 days.

(21) Appl. No.: 16/774,423

(22) Filed: Jan. 28, 2020

(65) Prior Publication Data

US 2020/0239521 A1    Jul. 30, 2020

(30) Foreign Application Priority Data

Jan. 28, 2019    (KR) .................. 10-2019-0010678

(51) Int. Cl.
| | |
|---|---|
| A61K 38/10 | (2006.01) |
| C07K 7/08 | (2006.01) |
| A61P 35/00 | (2006.01) |
| A61K 47/62 | (2017.01) |
| A61K 38/00 | (2006.01) |

(52) U.S. Cl.
CPC ............... *C07K 7/08* (2013.01); *A61K 47/62* (2017.08); *A61P 35/00* (2018.01); *A61K 38/00* (2013.01)

(58) Field of Classification Search
None
See application file for complete search history.

(56) References Cited

U.S. PATENT DOCUMENTS 8,877,889 B2 * 11/2014 Kim .................. A61P 35/00 530/325

FOREIGN PATENT DOCUMENTS

| JP | 4524359 B2 | 8/2010 |
|---|---|---|
| KR | 1020090118868 A | 11/2009 |
| KR | 10-2012-0083376 A | 7/2012 |
| KR | 1020130060846 A | 6/2013 |

OTHER PUBLICATIONS

The UniProt entry Q13794 for human NOXA, downloaded May 6, 2021.*
Reynolds, Fred et al; "A functional proteomic method for biomarker discovery." PLoS ONE (2010) 6(7) e22471.*
Costa, Ana Filipa et al; "Targeting glycosylation: a new road for cancer drug discovery." Trends Canc. (2020) 6(9) p. 757-766.*
Wang, Hui et al; "Expression, pruification,a nd characterization of a neovasculature targeted rmhtnf-alpha in *Escherichia coli*." Protein Expression and Purrification (2006) 45 p. 60-65.*
English Translation of Decision to Grant Registration dated Dec. 2, 2020 for Korean Patent Application No. 10-2019-0010678, Kim et al., "Cell-killing peptide eMTD derived from Noxa," filed Jan. 28, 2019 (1 page).
Woo et al., "Effects of the BH3-only protein human Noxa on mitochondrial dynamics," FEBS Lett. 583(14):2349-2354 (2009).
Office Action dated Apr. 1, 2020, for Korean Patent Application No. 10-2019-0010678, filed on Jan. 28, 2019 (10 pages).

* cited by examiner

*Primary Examiner* — Fred H Reynolds
(74) *Attorney, Agent, or Firm* — Clark & Elbing LLP; Susan M. Michaud

(57) ABSTRACT

Disclosed herein is a cell death-inducing peptide that rapidly acts. The peptide is derived from Noxa protein and comprises 16 amino acid residues including MTD. The peptide is designated extended MTD (eMTD) because it contains the 10-mer MTD. eMTD rapidly exhibits potent necrotic cell death in various cell lines and, as such, can be applied to the treatment of various diseases including cancer when used in conjugation with peptides or materials for targeting specific cells.

16 Claims, 19 Drawing Sheets

Specification includes a Sequence Listing.

SEQUENCE LISTING

<160> NUMBER OF SEQ ID NOS: 31

<210> SEQ ID NO 1
<211> LENGTH: 20
<212> TYPE: PRT
<213> ORGANISM: Artificial Sequence
<220> FEATURE:
<223> OTHER INFORMATION: Synthetic Construct

<400> SEQUENCE: 1

Lys Leu Asn Phe Arg Gln Lys Leu Leu Asn Leu Ile Ser Lys Leu Phe
 1               5                  10                  15

Cys Ser Gly Thr
            20

<210> SEQ ID NO 2
<211> LENGTH: 16
<212> TYPE: PRT
<213> ORGANISM: Artificial Sequence
<220> FEATURE:
<223> OTHER INFORMATION: Synthetic Construct

<400> SEQUENCE: 2

Lys Leu Asn Phe Arg Gln Lys Leu Leu Asn Leu Ile Ser Lys Leu Phe
 1               5                  10                  15

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Lys Leu Leu Asn Leu Ile Ser Lys Leu Phe
 1               5                  10

<210> SEQ ID NO 4
<211> LENGTH: 54
<212> TYPE: PRT
<213> ORGANISM: Artificial Sequence
<220> FEATURE:
<223> OTHER INFORMATION: Synthetic Construct

<400> SEQUENCE: 4

Met Pro Gly Lys Lys Ala Arg Lys Asn Ala Gln Pro Ser Pro Ala Arg
 1               5                  10                  15

Ala Pro Ala Glu Leu Glu Val Glu Cys Ala Thr Gln Leu Arg Arg Phe
                20                  25                  30

Gly Asp Lys Leu Asn Phe Arg Gln Lys Leu Leu Asn Leu Ile Ser Lys
            35                  40                  45

Leu Phe Cys Ser Gly Thr
                50

<210> SEQ ID NO 5
<211> LENGTH: 3
<212> TYPE: PRT
<213> ORGANISM: Artificial Sequence
<220> FEATURE:
<223> OTHER INFORMATION: Synthetic Construct

<400> SEQUENCE: 5

Arg Gly Asp
 1

```
<210> SEQ ID NO 6
<211> LENGTH: 13
<212> TYPE: PRT
<213> ORGANISM: Artificial Sequence
<220> FEATURE:
<223> OTHER INFORMATION: Synthetic Construct

<400> SEQUENCE: 6

Cys Asn Gly Arg Cys Val Ser Gly Cys Ala Gly Arg Cys
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Cys Asp Cys Arg Gly Asp Cys Phe Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Cys Arg Gly Asp Lys Gly Pro Asp Cys
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct

<400> SEQUENCE: 9

Arg Gly Asp Gly Trp Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct

<400> SEQUENCE: 10

Arg Gly Asp Phe Val
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Cys Arg Asn Gly Arg Gly Pro Asp Cys
1               5
```

```
<210> SEQ ID NO 12
<211> LENGTH: 7
<212> TYPE: PRT
<213> ORGANISM: Artificial Sequence
<220> FEATURE:
<223> OTHER INFORMATION: Synthetic Construct

<400> SEQUENCE: 12

Cys Gly Asn Lys Arg Thr Arg
1               5

<210> SEQ ID NO 13
<211> LENGTH: 31
<212> TYPE: PRT
<213> ORGANISM: Artificial Sequence
<220> FEATURE:
<223> OTHER INFORMATION: Synthetic Construct

<400> SEQUENCE: 13

Lys Asp Glu Pro Gln Arg Arg Ser Ala Arg Leu Ser Ala Lys Pro Ala
1               5                   10                  15

Pro Pro Lys Pro Glu Pro Lys Pro Lys Ala Pro Ala Lys Lys
            20                  25                  30

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Lys Leu Ala Lys Leu Ala Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15

Ile Phe Leu Leu Trp Gln Arg
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Cys Gly Asn Lys Arg Thr Arg Gly Cys
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17

Cys Arg Glu Ala Gly Arg Lys Ala Cys
1               5
```

```
<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Cys Ala Gly Arg Arg Ser Ala Tyr Cys
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Cys Leu Ser Asp Gly Lys Arg Lys Cys
1               5

<210> SEQ ID NO 20
<211> LENGTH: 12
<212> TYPE: PRT
<213> ORGANISM: Artificial Sequence
<220> FEATURE:
<223> OTHER INFORMATION: Synthetic Construct

<400> SEQUENCE: 20

Ser Val Ser Val Gly Met Lys Pro Ser Pro Arg Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Construct

<400> SEQUENCE: 21

Pro Arg Pro Ser Pro Lys Met Gly Val Ser Val Ser
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Construct

<400> SEQUENCE: 22

Thr Asp Ser Ile Leu Arg Ser Tyr Asp Trp Thr Tyr
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Cys Ser Asn Ile Asp Ala Arg Ala Cys
1               5
```

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Cys Gly Asn Ser Asn Pro Lys Ser Cys
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Cys Arg Gly Arg Arg Ser Thr
1               5

<210> SEQ ID NO 26
<211> LENGTH: 12
<212> TYPE: PRT
<213> ORGANISM: Artificial Sequence
<220> FEATURE:
<223> OTHER INFORMATION: Synthetic Construct

<400> SEQUENCE: 26

Phe Arg Pro Asn Arg Ala Gln Asp Tyr Asn Thr Asn
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic Construct

<400> SEQUENCE: 27

Ser Phe Ser Ile Ile His Thr Pro Ile Leu Pro Leu
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Cys Pro Ile Glu Asp Arg Pro Met Cys
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Cys Thr Pro Ser Pro Phe Ser His Cys
1               5

```
<210> SEQ ID NO 30
<211> LENGTH: 12
<212> TYPE: PRT
<213> ORGANISM: Artificial Sequence
<220> FEATURE:
<223> OTHER INFORMATION: Synthetic Construct

<400> SEQUENCE: 30

Thr Ser Pro Leu Asn Ile His Asn Gly Gln Lys Leu
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Synthetic Construct

<400> SEQUENCE: 31

Cys Arg Glu Lys Ala
1               5
```

NOXA-DERIVED, CELL DEATH-INDUCING PEPTIDE EMTD

SEQUENCE LISTING

The instant application contains a Sequence Listing which has been submitted electronically in ASCII format and is hereby incorporated by reference in its entirety. Said ASCII copy, created on Jan. 9, 2020 is named 50413-219001_Sequence_Listing_1.23.20_ST25 and is 6,973 bytes in size.

TECHNICAL FIELD

The present disclosure relates to a cell death-inducing peptide that acts rapidly and, more particularly, to a Noxa (SEQ ID NO: 4)-derived, cell death-inducing peptide comprising 16 amino acids inclusive of MTD (SEQ ID NO: 3). The peptide of the present disclosure rapidly exhibits potent necrotic cell death in various cell lines and, as such, can be applied to the treatment of various diseases including cancer when used in conjugation with peptides or materials for targeting specific cells.

BACKGROUND ART

There are various types of cell death. Active research into cell death has reported and defined various types of cell death, including: necrosis, which is the longest, passive concept of cell death; apoptosis, which is programmed, non-inflammatory cell death; necroptosis, which is a programmed form of necrosis; pyroptosis, which is a highly inflammatory form of programmed cell death; and ferroptosis, which is a type of programmed cell death dependent on intracellular iron ions. Although having different causes and characteristics, these types of cell death are not perfectly discriminated, but physiologically interact with each other, keeping homeostasis.

The regulation of cell death is very important. Aberrant regulation of cell death provokes various problems. Cancer is representative of diseases caused with the disruption of cell death regulation ability. Cancer exhibits abnormal cell growth with the potential to invade or spread to other parts of the body and is composed mainly of cells in which normal cell death functions do not work. A variety of autoimmune diseases results from failure to regulate cell death. When inflammatory cells cannot move elsewhere or a number of inflammatory cells remain due to failure to regulate cell death, inflammation may continue beyond what is necessary.

Broad spectrums of drugs that induce cell death are already used. Representative among the drugs are anticancer agents. Many anticancer agents take necrotic and apoptotic mechanisms in treating cancer. By way of example, there are medications that induce cell death through alkylation (e.g., cisplatin, etoposide, etc.) and medications used as metabolic antagonists (e.g., methotrexate, fluorouracil, etc.). Such medications are many also applied to the treatment of autoimmune diseases including rheumatoid arthritis (methotrexate), lupus (cyclophosphamide), and multiple sclerosis (cyclophosphamide).

Noxa (SEQ ID NO: 4) is an apoptotic protein. Noxa (SEQ ID NO: 4) expression can be induced in a p53-dependent manner upon DNA damage and genotoxic stress. Noxa (SEQ ID NO: 4) can also be induced in a p53-independent manner by alternative mechanisms including hypoxic condition and proteasome inhibition. The Bcl-2 homology 3 (BH3) domain of Noxa (SEQ ID NO: 4) binds Mcl-1 and Bcl2A1 to inactivate their anti-apoptotic activities. Consequently, BAX and BAK proteins are activated, causing cytochrome-c to leak into the cytosol, where the caspase system completes the apoptotic process.

DETAILED DESCRIPTION OF THE INVENTION

Technical Problem

A purpose of the present disclosure is to provide a necrosis-inducing peptide specific for cancer cells.

Another purpose of the present disclosure is to a polynucleotide coding for a necrosis-inducing peptide specific for cancer cells.

Another purpose of the present disclosure is to provide a recombinant vector carrying a polynucleotide coding for a necrosis-inducing peptide specific for cancer cells.

Another purpose of the present disclosure is to provide a cell transformed with a recombinant vector carrying a polynucleotide coding for a necrosis-inducing peptide specific for cancer cells.

Another purpose of the present disclosure is to provide a pharmaceutical composition, comprising a polynucleotide coding for a necrosis-inducing peptide specific for cancer cells, for prevention or treatment of cancer.

Another purpose of the present disclosure is to provide a use of a necrosis-inducing peptide specific for cancer cells in preventing or treating cancer.

Another purpose of the present disclosure is to provide a method for preventing or treating cancer, using a necrosis-inducing peptide specific for cancer cells.

Another purpose of the present disclosure is to provide a method for preparing a necrosis-inducing peptide specific for cancer cells.

Technical Solution

Disclosed is a peptide that induces rapid and potent necrosis in cells. Intensive and through research conducted by the present inventors resulted in the finding that extended MTD (eMTD; SEQ ID NO: 1), derived from Noxa (SEQ ID NO: 4), comprising the mitochondria targeting domain (MTD; SEQ ID NO: 3) can kill cancer cells. In this regard, the present inventors successfully extended the MTD (SEQ ID NO: 3) to construct a peptide capable of inducing cell death without being fused to a cell-penetrating peptide or other targeting peptides. The amino acid sequence of the peptide is derived from that of Noxa protein (SEQ ID NO: 4) and consists of at least 16 amino acids.

Accordingly, the present disclosure pertains to a cell death-inducing peptide using eMTD (SEQ ID NO: 1), a polynucleotide coding for the same, a recombinant vector carrying the polynucleotide, a transformed cell transformed with the recombinant vector, and a pharmaceutical composition comprising the peptide Hereinafter, a detailed description will be given of the present disclosure.

An aspect of the present disclosure pertains to a necrosis-inducing peptide.

In the present disclosure, the necrosis-inducing peptide may be a peptide comprising the amino acid sequence of SEQ ID NO: 1 or 2.

In the present disclosure, the necrosis-inducing peptide may further comprise a tumor-homing peptide (THP) conjugated at the N- and/or C-terminal thereof.

In the present disclosure, the tumor-homing peptide may comprise an amino acid sequence selected from the amino acid sequences of SEQ ID NOS: 5 to 31, but is not limited thereto.

In the present disclosure, the tumor-homing peptide may be conjugated to the necrosis-inducing peptide via a linker, but without limitations thereto.

In the present disclosure, the linker may include as a connector an amino acid sequence so long as not to disturb the induction of necrosis or a chemical connecting group degradable within a cell.

Available are various linkers known in the art (Huston, et al., Methods in Enzymology, 203:46-88(1991) and Whitlow, et al., Protein Eng., 6:989(1993)). For example, the linker may be composed of 1 to 5 amino acids including glycine or serine and other amino acids.

TABLE 1

| SEQ ID NO. | Name | Sequencing List |
|---|---|---|
| 5 | RGD | RGD |
| 6 | NGR | CNGRCVSGCAGRC |
| 7 | RGD-4C | CDCRGDCFC |
| 8 | iRGD | CRGDKGPDC |
| 9 | RGDWK | RGDWK |
| 10 | Cilengitide | -RGDfV- |
| 11 | iNGR | CRNGRGPDC |
| 12 | Lyp-1(tLyp-1) | CGNKRTR |
| 13 | F3 | KDEPQRRSARLSAKPAPPKPEPKPKKAPAKK |
| 14 | TMTP1 | KLAKLAK |
| 15 | IF7 | IFLLWQR |
| 16 | Lyp-1 | CGNKRTRGC |
| 17 | REA | CREAGRKAC |
| 18 | AGR | CAGRRSAYC |
| 19 | LSD | CLSDGKRKC |
| 20 | SP5-52 | SVSVGMKPSPRP |
| 21 | D-SP5 | PRPSPKMGVSVS |
| 22 | PC5-2 | TDSILRSYDWTY |
| 23 | 4R22 | CSNIDARAC |
| 24 | GX1 | CGNSNPKSC |
| 25 | RGR | CRGRRST |
| 26 | DUP-1 | FRPNRAQDYNTN |
| 27 | SP94 | SFSIIHTPILPL |
| 28 | RPMrel | CPIEDRPMC |
| 29 | TCP-1 | CTPSPFSHC |
| 30 | HN-1 | TSPLNIHNGQKL |
| 31 | CREKA | CREKA |

As used herein, the term "peptide" refers to a linear molecule which is formed as amino acid residues are bonded to each other via a peptide bond.

The peptide in the present disclosure may be directly synthesized in a chemical manner using solid-phase peptide synthesis or may be biologically prepared by inserting DNA encoding the peptide a vector, expressing the DNA through transcription and translation in vitro, and purifying the peptide, but without limitations thereto.

Another aspect of the present disclosure pertains to a polynucleotide coding for the necrosis-inducing peptide.

In the present disclosure, the polynucleotide may be chemically synthesized with the aid of an automated synthesizer on the basis of codons of the necrosis-inducing peptide or may be prepared through PCR amplification or transcription of the synthesized gene, but without limitations thereto.

In the present disclosure, the polynucleotide may encode a necrosis-inducing peptide including the amino acid sequence of SEQ ID NO: 1 or 2.

In the present disclosure, the necrosis-inducing peptide may further comprise a tumor-homing peptide (THP) conjugated to the N- and/or C-terminal thereof.

In the present disclosure, the tumor-homing peptide may comprise an amino acid selected from SEQ ID NOS: 5 to 31, but is not limited thereto.

In the present disclosure, the tumor-homing peptide may be conjugated to the necrosis-inducing peptide via a linker, but without limitations thereto.

In the present disclosure, the linker may include as a connector an amino acid sequence so short as not to disturb the induction of necrosis or a chemical connecting group degradable within a cell.

Another aspect of the present disclosure pertains to a recombinant vector carrying a polynucleotide coding for a necrosis-inducing peptide.

In the present disclosure, the polynucleotide may encode a necrosis-inducing peptide including the amino acid sequence of SEQ ID NO: 1 or 2.

In the present disclosure, the necrosis-inducing peptide may further comprise a tumor-homing peptide (THP) conjugated to the N- and/or C-terminal thereof.

In the present disclosure, the tumor-homing peptide may comprise an amino acid selected from SEQ ID NOS: 5 to 31, but is not limited thereto.

In the present disclosure, the tumor-homing peptide may be conjugated to the necrosis-inducing peptide via a linker, but without limitations thereto.

In the present disclosure, the linker may include as a connector an amino acid sequence so short as not to disturb the induction of necrosis or a chemical connecting group degradable within a cell.

As used herein, the term "vector" refers to a means for expressing a gene of interest in a host cell. Examples of the vector include plasmid vectors, cosmid vectors, and viral vectors such as bacteriophage vectors, adenovirus vectors, retroviral vectors, and adeno-associated virus vectors. For use as the recombinant vector, a plasmid (e.g., pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), a phage (e.g., λgt4λB, λ-Charon, λΔz1, M13, etc.) or a virus (e.g., SV40, etc.) may be manipulated.

The recombinant vector may be typically constructed into a cloning or expression vector. The expression vector may be a typical one that is used in the art to express a foreign protein in plants, animals, or microorganisms. The recombinant vector may be constructed in various manners known in the art.

For the construction of the recombinant vector, a prokaryote or eukaryote may serve as a host. For example, in the case where an expression vector is used with a eukaryote serving as a host, the vector generally includes a potent promoter capable of performing transcription (e.g., pL$^\lambda$ promoter, CMV promoter, trp promoter, lac promoter, tac promoter, T7 promoter, etc.), a ribosomal binding site for initiating translation, and transcription/translation stop sequences. For eukaryotes serving as hosts, the expression vector is constructed to have a replication origin examples of which include an f1 replication origin, an SV40 replication origin, a pMB1 replication origin, an adeno replication origin, an AAV replication origin, and a BBV replication origin, but is not limited thereto. In addition, the vector may employ a promoter derived from the genome of mammalian cells (e.g., a metallothionein promoter) or from mammalian cell-grown virus (e.g., an adenovirus late promoter, a vaccinia virus 7.5K promoter, an SV40 promoter, a cytomegalovirus promoter, and an HSV tk promoter) and typically contains a polyadenylation sequence as a transcription stop sequence.

Another aspect of the present disclosure pertains to a cell transformed with a recombinant vector carrying a polynucleotide coding for a necrosis-inducing peptide specific for cancer cells.

In the present disclosure, the polynucleotide may encode a necrosis-inducing peptide including the amino acid sequence of SEQ ID NO: 1 or 2.

In the present disclosure, the necrosis-inducing peptide may further comprise a tumor-homing peptide (THP) conjugated to the N- and/or C-terminal thereof.

In the present disclosure, the tumor-homing peptide may comprise an amino acid selected from SEQ ID NOS: 5 to 31, but is not limited thereto.

In the present disclosure, the tumor-homing peptide may be conjugated to the necrosis-inducing peptide via a linker, but without limitations thereto.

In the present disclosure, the linker may include as a connector an amino acid sequence so short as not to disturb the induction of necrosis or a chemical connecting group degradable within a cell.

Within the scope of the host cell used in the present disclosure, *E. coli*, yeasts, animal cells, plant cells, and insect cells fall, as exemplified by prokaryotic enterobacteriaceae strains including *E. coli* JM109, *E. coli* BL21, *E. coli* RR1, *E. coli* LE392, *E. coli* B, *E. coli* X 1776, *E. coli* W3110, *Bacillus* spp. such as *Bacillus subtilis* and *Bacillus churingiensis*, *Salmonella typhimurium*, *Seratia marcescens*, and various *Pseudomonas* spp. As eukaryotic host cells to be transformed, yeast (Saccharomyce cerevisiae), insect cells, plant cells, and animal cells may be used. Examples of the eukaryotic cells include Sp2/0, CHO (Chinese hamster ovary) K1, CHO DG44, PER.C6, W138, BHK, COS7, 293, HepG2, Huh7, 3T3, RIN, and MDCK cell lines, but are not limited thereto.

The delivery (introduction) of the polynucleotide or the recombinant vector carrying the same into a host cell may be achieved using a delivery method well known in the art. When the host cell is prokaryotic, the delivery method may be a CaCl$_2$ method or electroporation. For eukaryotes as host cells, microinjection, calcium phosphate precipitation, electroporation, liposome-mediated transfection, or genetic bombardment may be used, without limitations thereto.

Selection of the transformed host cells may be easily performed according to well-known methods using the phenotypes expressed by selection markers used. For example, when a gene resistant to a specific antibiotic is used as a selection marker, the transformant may be easily selected by being cultured on a medium containing the antibiotic.

Another aspect of the present disclosure pertains to a pharmaceutical composition for prevention or treatment of cancer, the composition comprising a polynucleotide coding for a necrosis-inducing peptide specific for cancer cells.

In the present disclosure, the necrosis-inducing peptide may further comprise a tumor-homing peptide (THP) conjugated to the N- and/or C-terminal thereof.

In the present disclosure, the tumor-homing peptide may comprise an amino acid selected from SEQ ID NOS: 5 to 31, but is not limited thereto.

In the present disclosure, the tumor-homing peptide may be conjugated to the necrosis-inducing peptide via a linker, but without limitations thereto.

In the present disclosure, the linker may include as a connector an amino acid sequence so short as not to disturb the induction of necrosis or a chemical connecting group degradable within a cell.

In the present disclosure, the cancer may be lung cancer, breast cancer, liver cancer, melanoma, stomach cancer, pancreatic cancer, colorectal cancer, ovarian cancer, renal cell carcinoma, prostate cancer, or brain tumor, but is not limited thereto.

The content of the necrosis-inducing peptide as an effective ingredient in the composition may be appropriately adjusted depending on usage form and purpose, patient's condition, kinds and severity of symptoms and may range from 0.001 to 99.9% by weight or from 0.1 to 99.9% by weight, preferably from 0.1 to 50% by weight or from 0.1 to 40% by weight, based on the weight of the solid content, but without limitations thereto.

The pharmaceutical composition according to the present disclosure may be administered via various routes to mammals including humans. Administration may be conducted in any typical mode. For example, the composition may be administered via an oral, dermal, intravenous, intramuscular, or subcutaneous route. Alternatively, the composition may take a topical spray form administrable intranasally.

According to typical methods, the composition of the present disclosure may be formulated into oral dosage forms such as powders, granules, tablets, capsules, ointments, suspensions, emulsions, syrups, aerosols, etc., or parenteral dosage forms such as transdermal agents, sprays, suppositories, and sterile injections.

In addition to the cancer cell-specific, necrosis-inducing fusion peptide, the pharmaceutical composition of the present disclosure may further comprise a pharmaceutically suitable and biologically acceptable auxiliary agent such as carriers, excipients, and diluents.

Examples of the carrier, excipient, or diluent available in the pharmaceutical composition of the present disclosure include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil.

For formulating the composition, a typical diluent or excipient, such as filler, a thickener, a binder, a humectant, a disintegrant, a surfactant, and the like, may be used. Solid formulations for oral administration include tablets, pills, powder, granules, and capsules, and can be prepared by mixing the above extract with one or more excipients such as starch, calcium carbonate, sucrose, lactose, or gelatin. In addition, lubricants such as magnesium stearate and talc can be used instead of simple excipients.

Liquid formulations for oral administration include a suspension, a liquid for internal use, an emulsion, syrup, and a gel, and frequently used water, liquid paraffin and other excipients such as humectants, sweeteners, aromatics, and preservatives can also be used.

In the formulations for non-oral administration, a sterilized aqueous solution, a non-aqueous solvent, a suspension, an emulsion, a lyophilized formulation, a suppository, and a transcutaneous formulation are included.

Propylene glycol, polyethylene glycol, vegetable oil, such as olive oil, and injectable esters, such as ethyloleate, can be used as a non-aqueous solvent or a suspension. The base for suppository includes Witepsol, Macrogol, Tween 61, cacao oil, laurin oil, glycerol, and gelatin.

The pharmaceutical composition of the present disclosure may be administered to humans, alone or in mixture with pharmaceutical carriers selected in consideration of general protocols and the standard pharmaceutical practice.

By way of example, the pharmaceutical composition of the present disclosure may be orally, buccally, or sublingually administered in the form of tablets containing starch or lactose, in the form of capsules containing the composition alone or in mixture with excipients, or in the form of elixirs or suspensions with chemicals for taste masking or coloration.

Such liquid formulations can be formulated with pharmaceutically acceptable additives such as suspending agents (e.g., methyl cellulose, semisynthetic glyceride such as Witepsol, a mixture of apricot kernel oil and PEG-6 esters, and a glyceride mixture such as PEG-8 and caprylic/capric glyceride mixture).

The administration dose of the pharmaceutical composition of the present disclosure may vary depending on the age, weight, health status and seriousness of the disease of the patient, and the composition may be administered in a single dose or multiple discrete doses at regular time intervals a day, depending on the judgment of physicians or pharmacists.

For instance, daily dose of the effective ingredient can be 0.1 to 500 mg/kg, and preferably 0.5 to 300 mg/kg. The above dose is only an average value, and the dose can be higher or lower depending on the personal differences.

It is preferable to have the above dose range not only because a lower daily dose of the pharmaceutical composition of the present disclosure does not guarantee a meaningful effect, but also because a higher dose is economically disadvantageous and may cause undesirable side effects.

Advantageous Effects

Disclosed herein is a cell death-inducing peptide that rapidly acts. The peptide is derived from Noxa protein (SEQ ID NO: 4) and comprises 16 amino acid residues including MTD (SEQ ID NO: 3). The peptide is designated extended MTD (eMTD; SEQ ID NO: 1) because it contains the 10-mer MTD (SEQ ID NO: 3). eMTD (SEQ ID NO: 1) rapidly exhibits potent necrotic cell death in various cell lines and, as such, can be applied to the treatment of various diseases including cancer when used in conjugation with peptides or materials for targeting specific cells.

Figure 9:
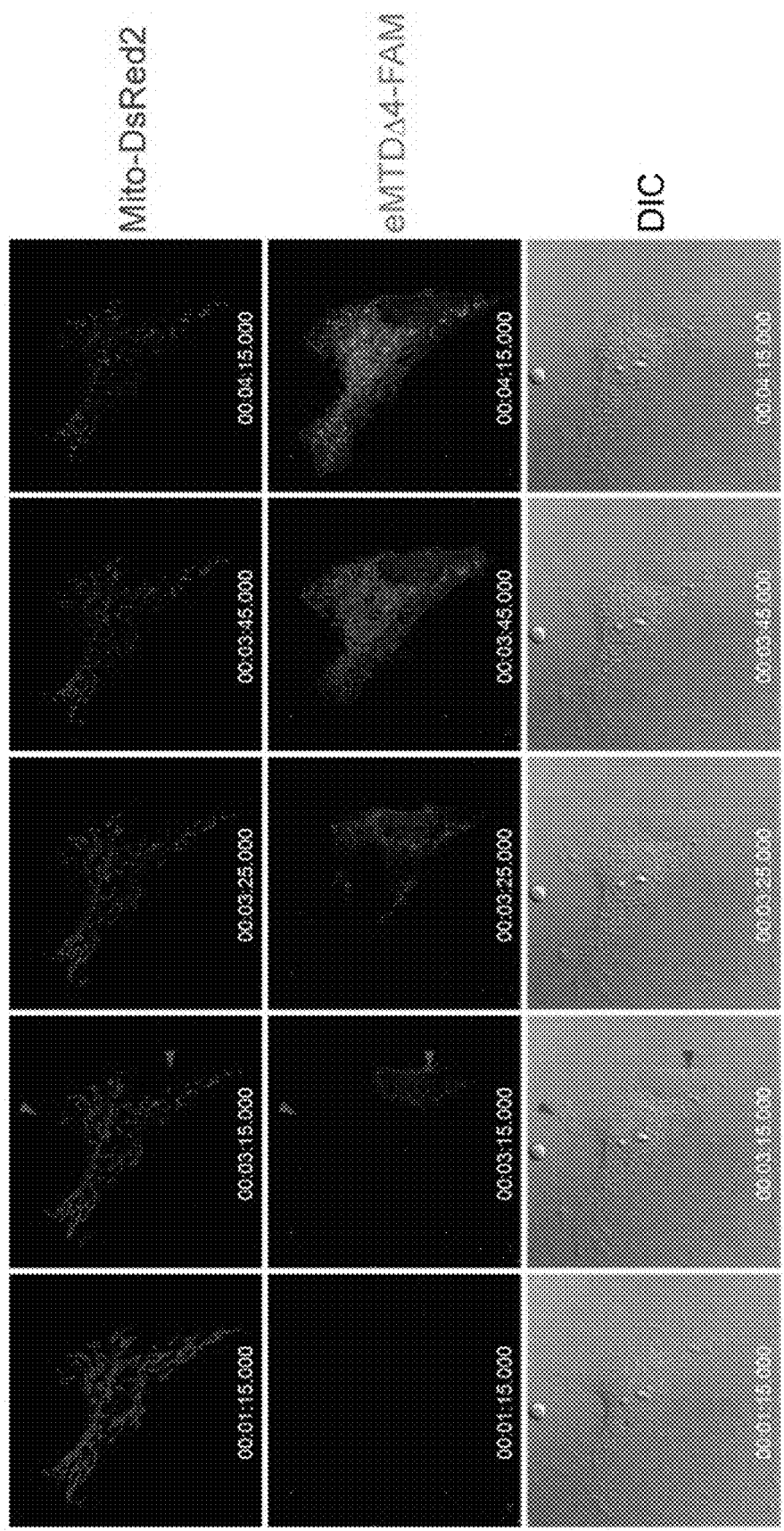
Figure 10A:
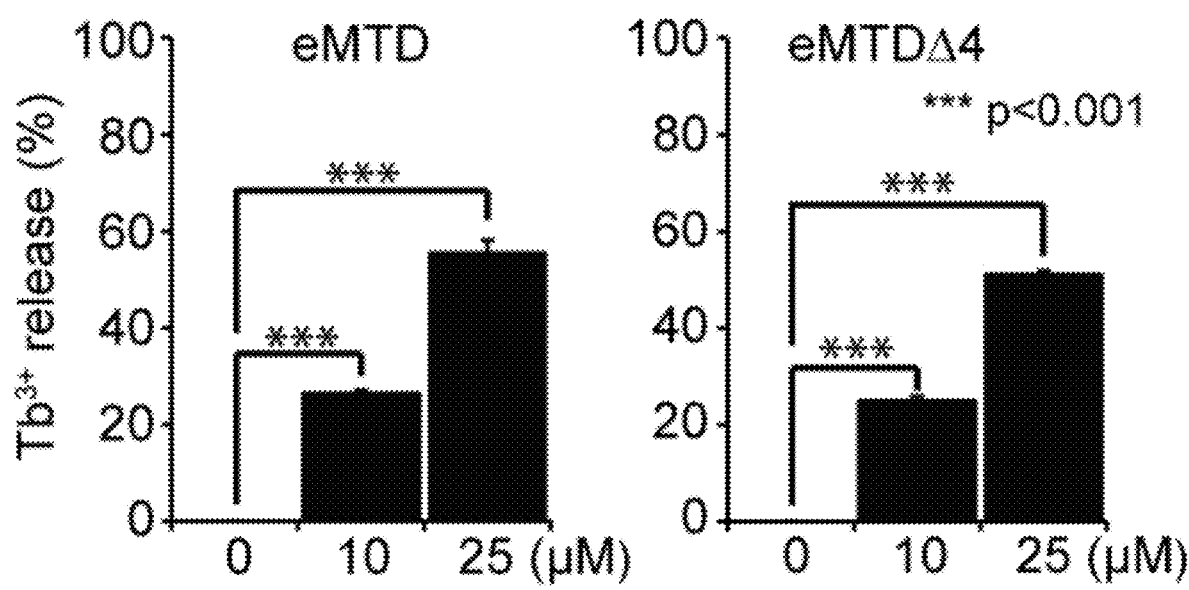

μM of eMTDΔ4 (SEQ ID NO: 2) according to an embodiment of the present disclosure;

FIG. 9 shows time-lapse, confocal microscopic images of Hela cells treated with the peptide eMTDΔ4 (SEQ ID NO: 2) conjugated with a fluorescent (Fluorescein; FAM) according to an embodiment of the present embodiment;

FIG. 10a shows degrees of damage on the lipid membrane of liposomes as analyzed by two-step assay according to an embodiment of the present disclosure.

Figure 10B:
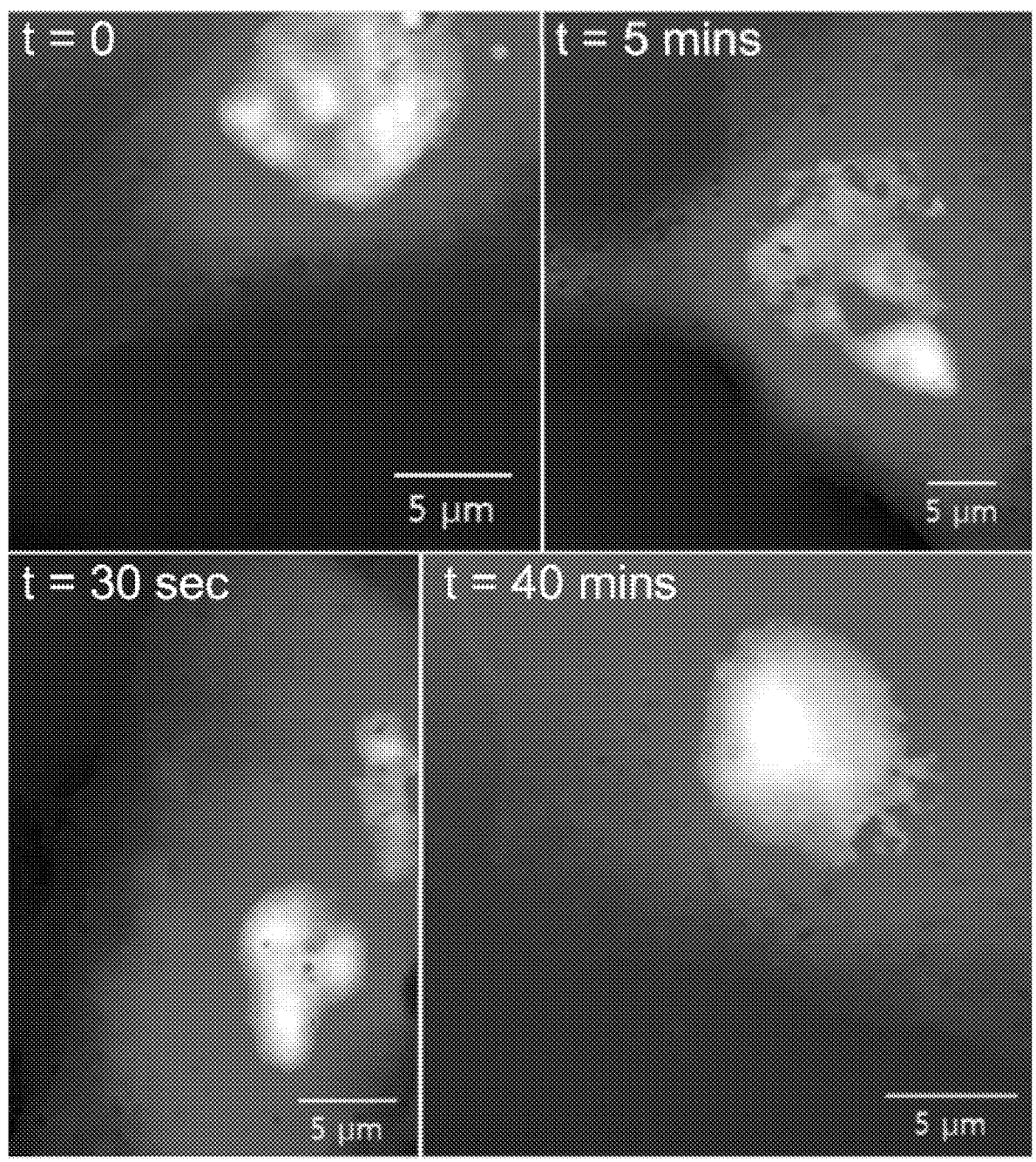
Figure 10C:
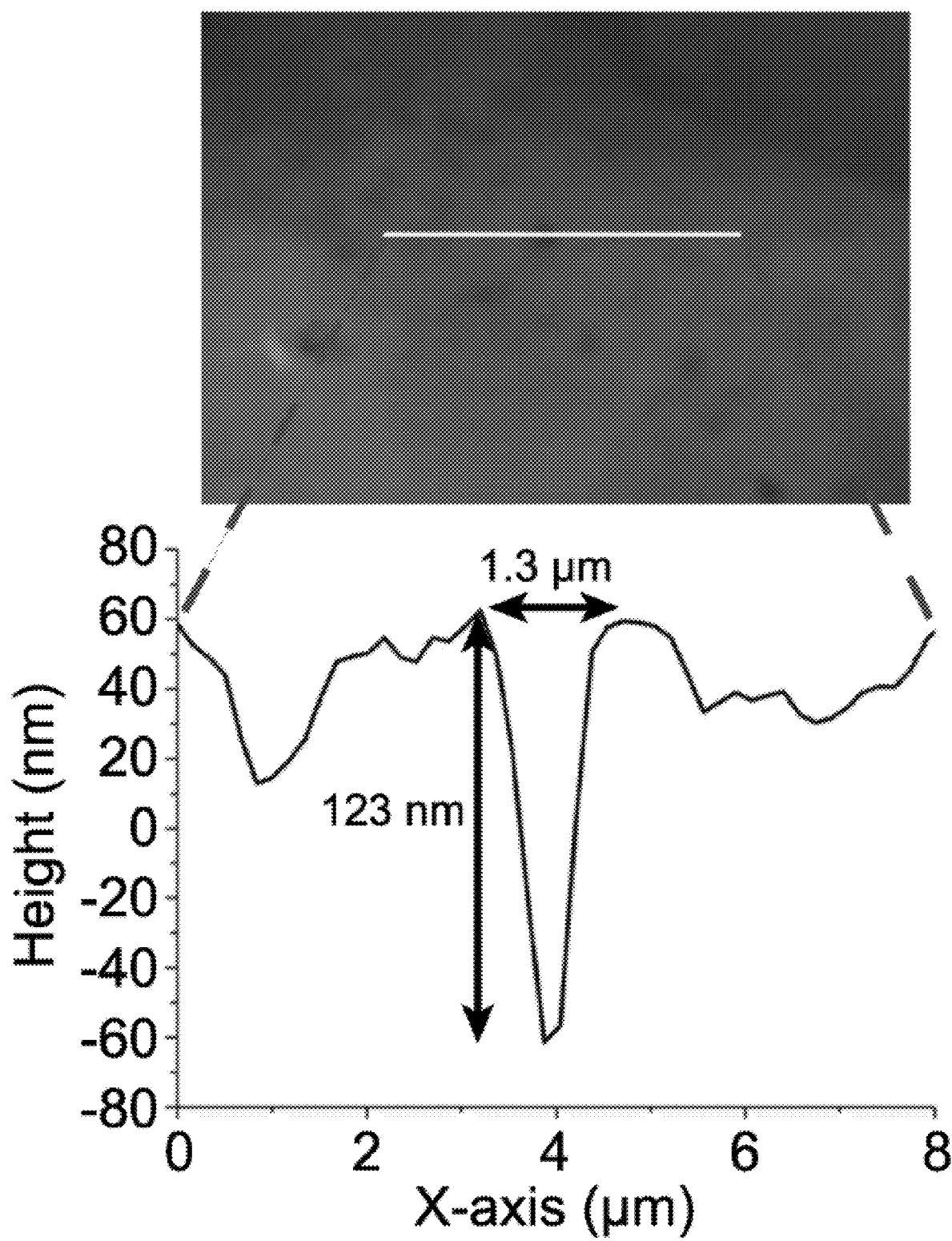
Figure 10D:
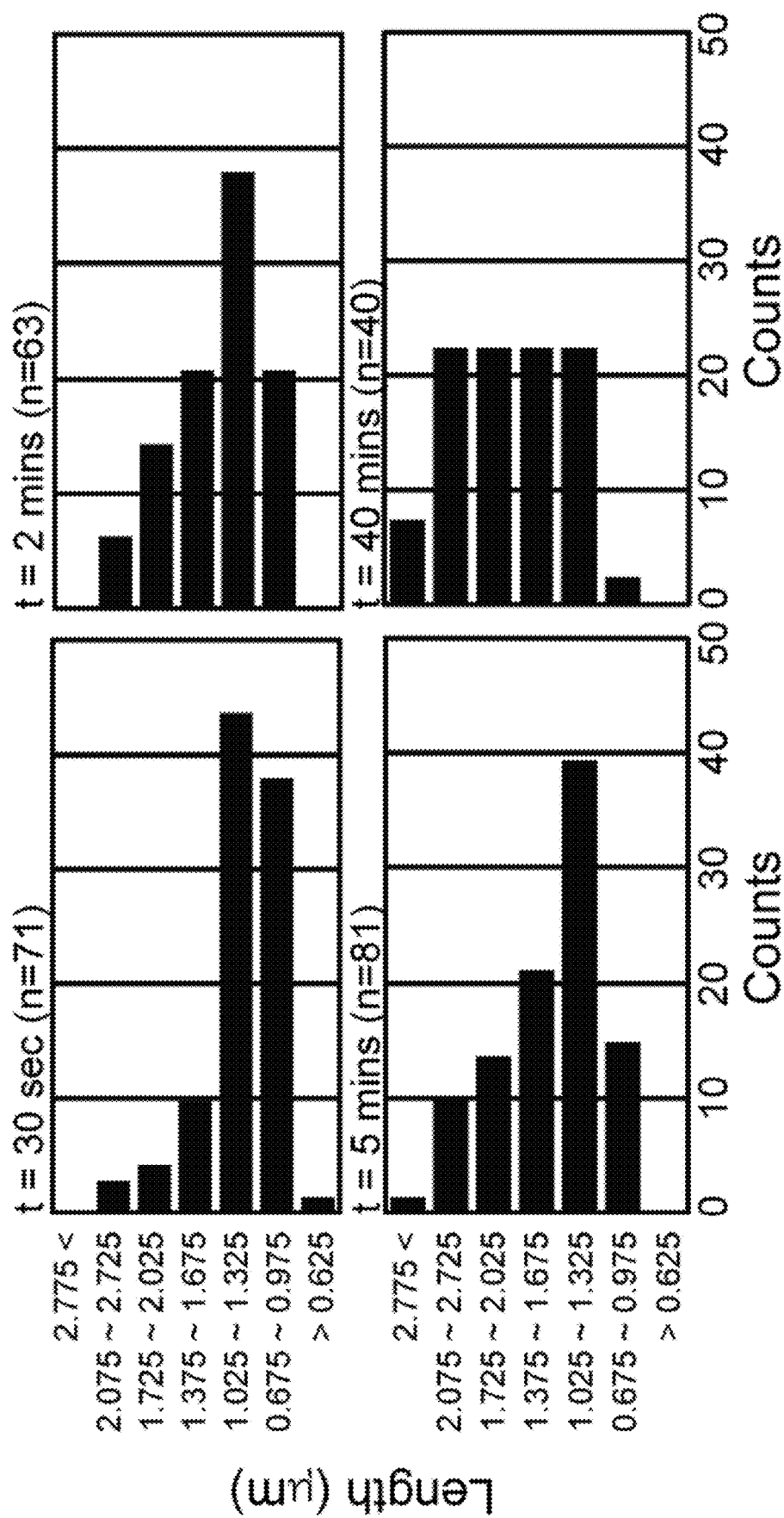

FIG. 10b shows the damage of the peptide eMTDΔ4 (SEQ ID NO: 2) on the cell membrane in time-lapse atomic force microscopic images according to an embodiment of the present disclosure;

FIG. 10c shows the damage of the peptide eMTDΔ4 (SEQ ID NO: 2) on the cell membrane and the depth of the cell membrane damage in time-lapse atomic force microscopic images according to an embodiment of the present disclosure; and FIG. 10d shows statistical data of damage, photographically taken by atomic force microscopy, of the peptide eMTDΔ4 (SEQ ID NO: 2) on the cell membrane.

MODE FOR CARRYING OUT THE INVENTION

A better understanding of the present disclosure may be obtained through the following examples which are set forth to illustrate, but are not to be construed as limiting the present disclosure.

EXAMPLE 1: PEPTIDE SYNTHESIS

Peptide synthesis was entrusted to Anygen in which peptides were synthesized using solid-phase peptide synthesis, purified by high-capacity HPLC, dissolved at a concentration of 1 mM in 50% aqueous DMSO (dimethyl sulfoxide) solution, and then stored at −20° C. Amino acids sequences of the peptides are given in Table 2, below.

TABLE 2

| SEQ ID NO: | Name | Sequencing List |
|---|---|---|
| 1 | eMTD | KLNFRQKLLNLISKLFCSGT |
| 2 | eMTDΔ4 | KLNFRQKLLNLISKLF |
| 3 | MTD | KLLNLISKLF |
| 4 | Noxa | MPGKKARKNAQPSPARAPAELEVECAT QLRRFGDKLNFRQKLLNLISKLFCSGT |

EXAMPLE 2: CULTURE OF CANCER CELL LINE

Individual cell lines (HeLa, CT26, and B16F10) were purchased from the Korean Cell Line Bank. Dulbecco's modified Eagle's medium (DMEM), trypsin-EDTA, fetal bovine serum (FBS), and Hank's balanced salt solution (HBSS) were products from Gibco (Thermo Fisher).

Each of the cell lines was cultured in DMEM supplemented with 10% FBS in an incubator maintained at 37° C. and 5% 002.

EXAMPLE 3: ASSAY FOR CELL DEATH INDUCTION OF EMTD (SEQ ID NO: 1) PEPTIDE 3-1. Assay for Activity of Cell Death Induction in Uterine Cervical Cancer For use in assaying the peptides eMTD (SEQ ID NO: 1) and eMTDΔ4 (SEQ ID NO: 2) synthesized in Example 1 for activity of inducing cell death, the cell line HeLa was grown to about 90% confluency in 96-well plates. The cells were washed once with HBSS buffer before treatment with the peptides of the present disclosure eMTD (SEQ ID NO: 1) and eMTDΔ4 (SEQ ID NO: 2) at concentrations of 0, 20, and 40 for one hour. Thereafter, the cells were incubated with an MTS assay agent (Promega) for one hour, followed by reading absorbance to calculate relative viability of cells. The results are given in FIG. 1 and Table 3.

TABLE 3

| | | 0 μM | 20 μM | 40 μM |
|---|---|---|---|---|
| fl-Noxa (SEQ ID NO: 4) | Viability (%) | 100 | 101 | 106 |
| | Standard deviation | 0.079 | 0.037 | 0.050 |
| eMTD (SEQ ID NO: 1) | Viability (%) | 100 | 61 | 63 |
| | Standard deviation | 0.079 | 0.007 | 0.023 |
| eMTDΔ4 (SEQ ID NO: 2) | Viability (%) | 100 | 53 | 40 |
| | Standard deviation | 0.079 | 0.082 | 0.044 |

Figure 1:
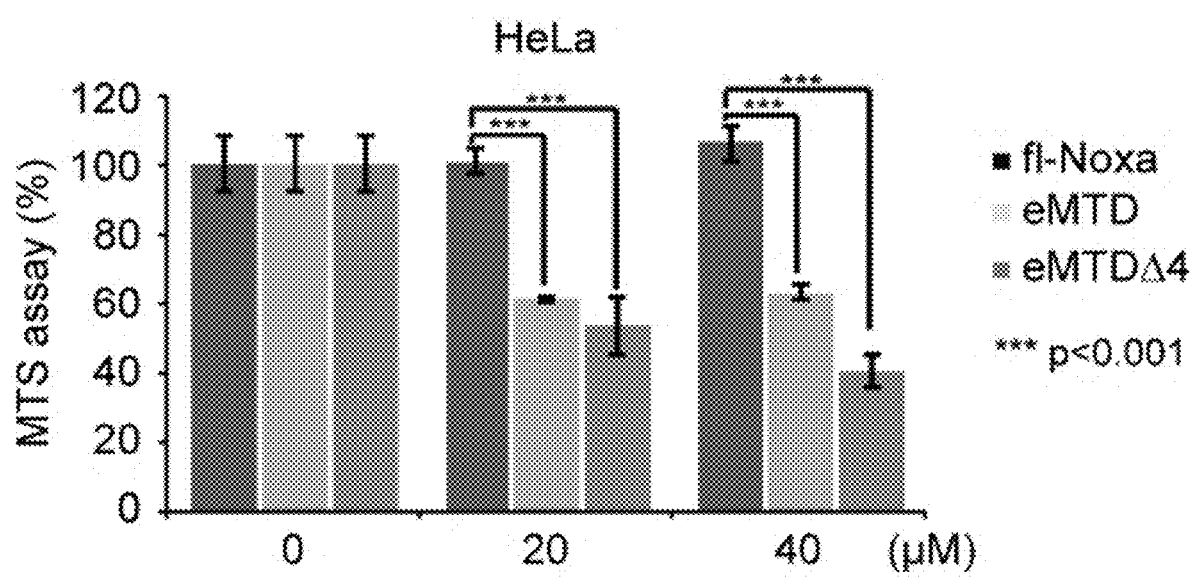
FIG. 1 shows relative cell viability after treatment of HeLa cell line with eMTD (SEQ ID NO: 1) peptide or eMTDΔ4 (SEQ ID NO: 2) peptide according to an embodiment of the present disclosure, as measured by MTS assay.

As is understood from the data of FIG. 1 and Table 3, eMTD (SEQ ID NO: 1) and eMTDΔ4 (SEQ ID NO: 2) peptides exhibit potent cell death activity.

3-2. Microscopic Observation of Morphological Change in Cells

In order to observe morphological changes in cells in detail, the cells were incubated with 20 μM of the peptide eMTDΔ4 (SEQ ID NO: 2) and observed with the aid of a microscope (Leica). The results are depicted in FIG. 2.

Figure 2:
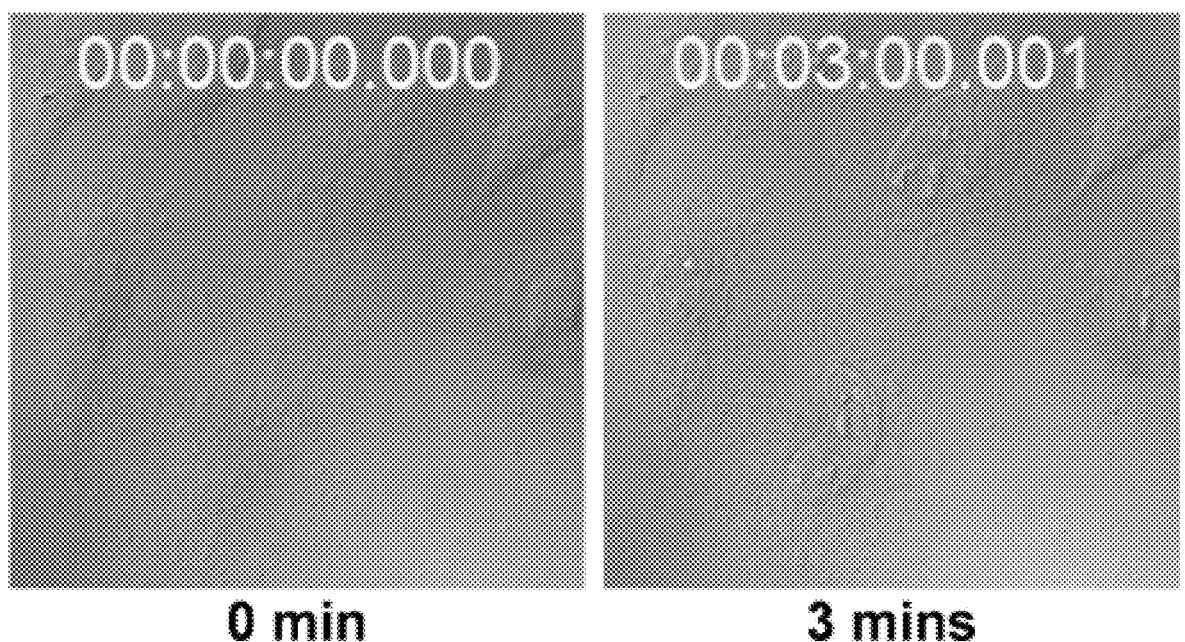
FIG. 2 shows microscopic images of HeLa cells after or before treatment with 20 μM of eMTDΔ4 (SEQ ID NO: 2) for 3 min.

As shown in FIG. 2, most of the cells were observed to undergo necrosis with the consequent rupture of cell membranes after 3 min of incubation with the peptide.

3-3. Assay for Activity of Cell Death Induction in Other Cancer Cell Lines

Examination was made to see whether the peptide has the activity of inducing cell death in other cancer cell lines. In this regard, the cancer cell lines HeLa, CT26, and B16F10 were treated with eMTDΔ4 (SEQ ID NO: 2) at concentrations of 0, 20, and 40 μM. Cell viability was measured by MTS assay and the results are given in FIG. 3 and Table 4.

TABLE 4

| eMTDΔ4 (SEQ ID NO: 2) | | HeLa | CT26 | B16F10 |
|---|---|---|---|---|
| 0 μM | Viability (%) | 100 | 100 | 100 |
| | Standard deviation | 5.72 | 11.81 | 7.73 |
| 10 μM | Viability (%) | 47 | 69 | 68 |
| | Standard deviation | 5.07 | 13.08 | 5.71 |
| 20 μM | Viability (%) | 11 | 21 | 33 |
| | Standard deviation | 0.98 | 0.69 | 3.99 |

Figure 3:
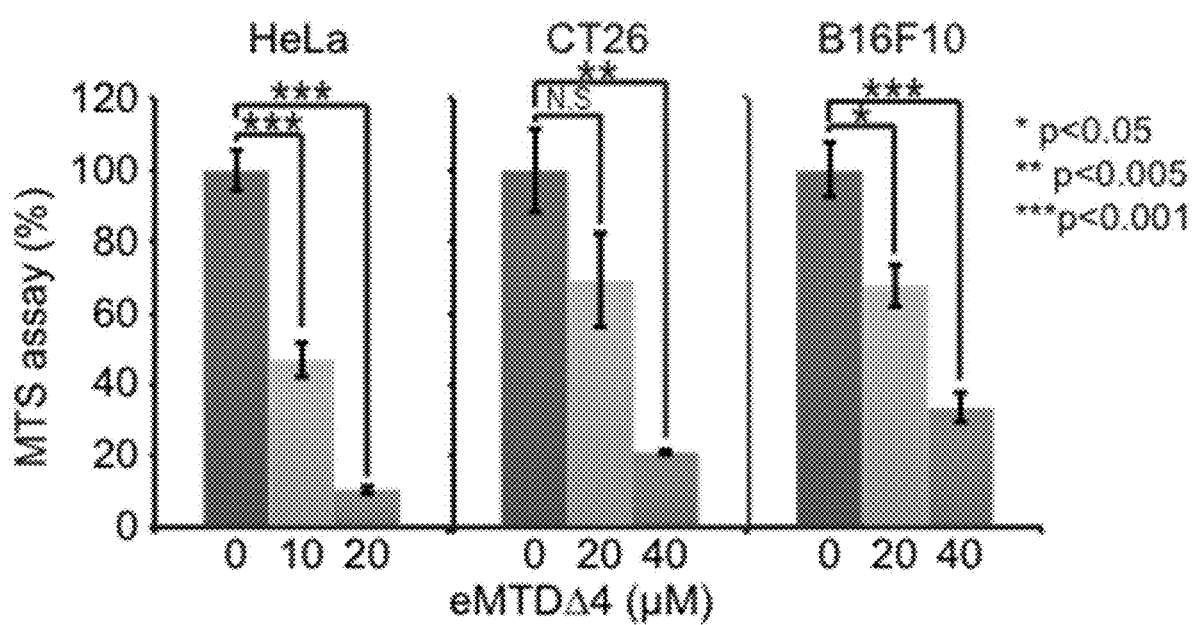
FIG. 3 shows relative cell viability after treatment of HeLa, CT26, and B16F10 cell lines with eMTDΔ4 (SEQ ID NO: 2) peptide according to an embodiment of the present disclosure, as measured by MTS assay.

As can be understood from the data of FIG. 3 and Table 4, the peptide eMTDΔ4 (SEQ ID NO: 2) was found to induce cell death in HeLa, which is a human uterine cervical cancer cell line as well as in CT26, which is derived from murine colon carcinoma, and B16F10, which is derived from murine melanoma cells.

EXAMPLE 4: INDUCTION OF CELL DEATH AND INTRACELLULAR CALCIUM LEVEL CHANGE BY PEPTIDE eMTDΔ4 (SEQ ID NO: 2)

In order to examine the mechanism in which the peptide eMTD (SEQ ID NO: 1) induces cell death in cancer cell lines, a change in intracellular calcium level, which is known as an important factor for cell death, was observed using the calcium indicator Fluo-4 under a confocal microscope (Leica).

In brief, HeLa cells were grown to about 70% confluency in a Lab-Tek chamber glass a day before the experiment. Immediately before the experiment, of the calcium indicator Fluo-4 was diluted to a concentration of 5 in HBSS. HeLa cells were incubated with the dilution for 10 min in an incubator and then treated with the peptide eMTDΔ4 (SEQ ID NO: 2). Results are given in FIGS. 4A and 4C.

Figure 4A:
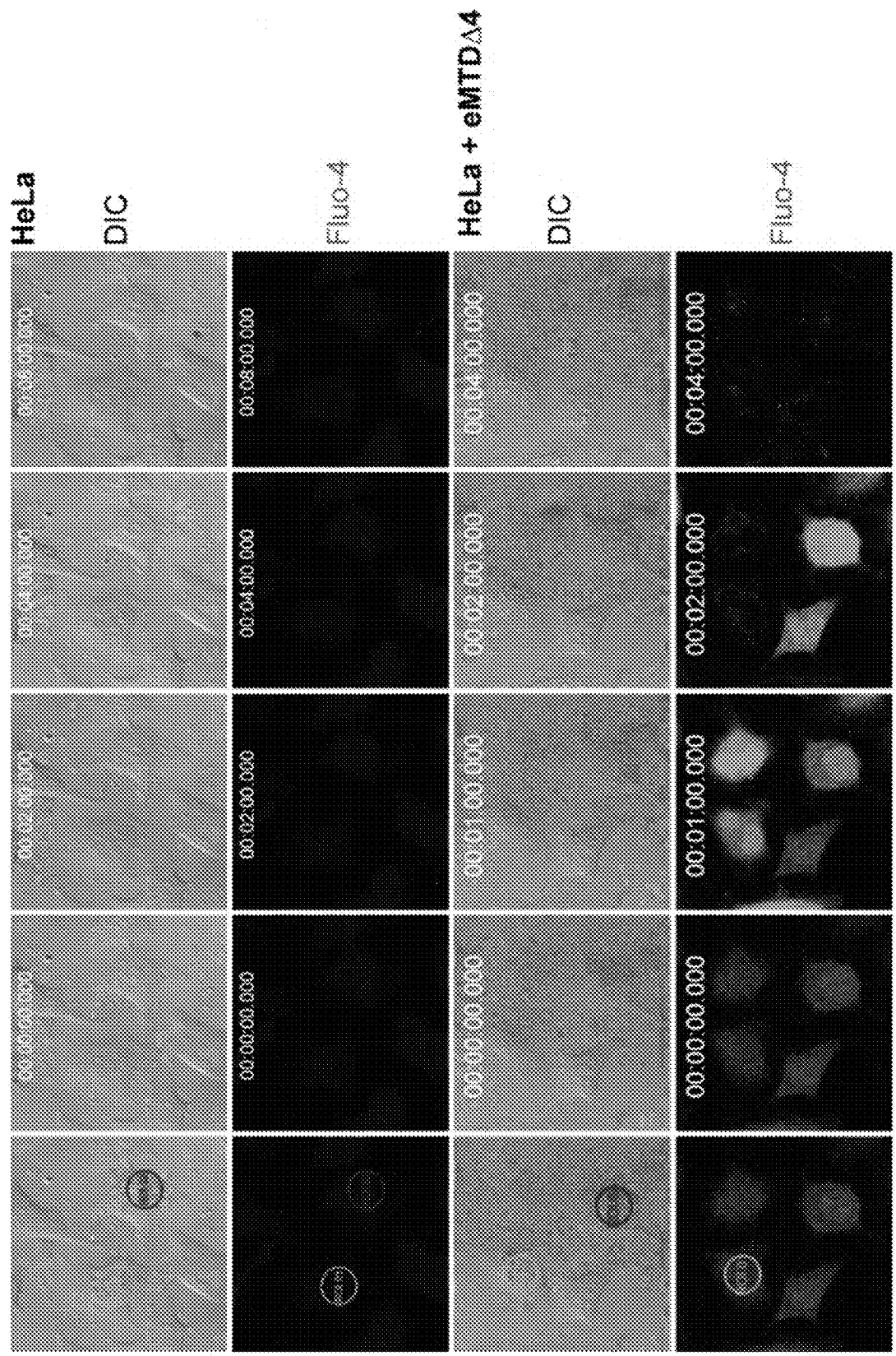
FIG. 4a shows time-lapse, confocal microscopic images of HeLa cells stained with the calcium indicator Fluo-4 and then treated with or without 20 μM of eMTDΔ4 (SEQ ID NO: 2) according to an embodiment of the present disclosure.
Figure 4B:
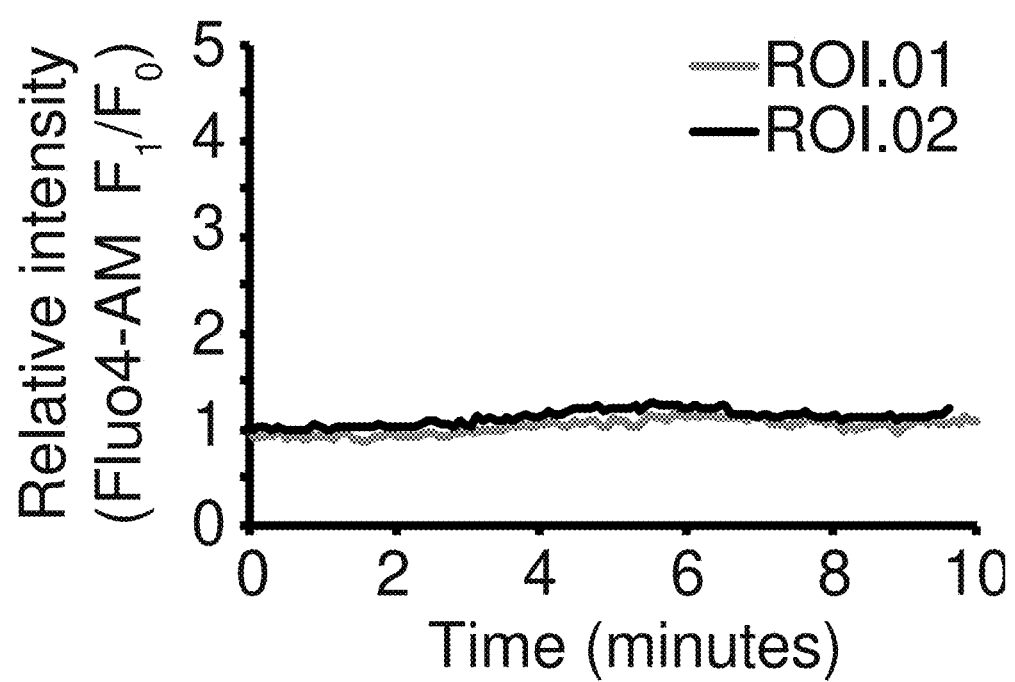
FIG. 4b is a graph showing Fluo-4 intensities within ROI (region of interest) of time-lapse confocal microscopic images of HeLa cells stained with the calcium indicator Fluo-4 without eMTDΔ4 (SEQ ID NO: 2) treatment according to an embodiment of the present disclosure.
Figure 4C:
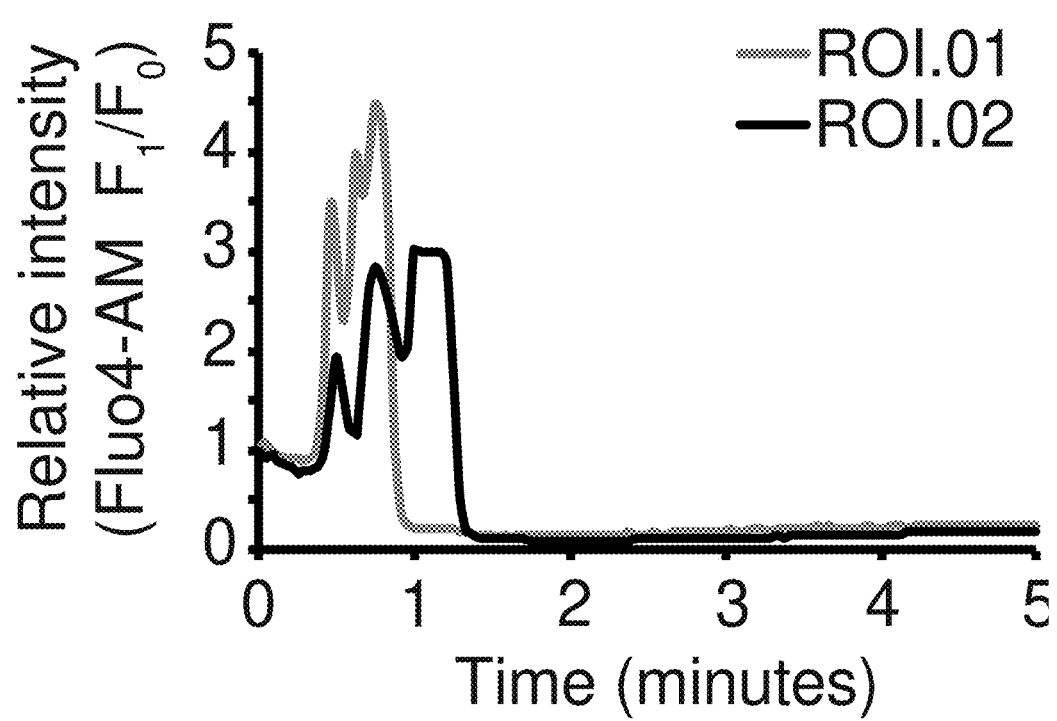
FIG. 4c is a graph showing Fluo-4 intensities within ROI (region of interest) of time-lapse confocal microscopic images of HeLa cells stained with the calcium indicator Fluo-4 and then treated with 20 of eMTDΔ4 (SEQ ID NO: 2) according to an embodiment of the present disclosure.

As shown in FIGS. 4A to 4C, almost no changes in intracellular calcium level were found in HeLa cells that had not been treated with the peptide. In contrast, the HeLa cells were observed to allow calcium influx into the cytosols thereof within less than one min after treatment with the peptide eMTDΔ4 (SEQ ID NO: 2). In this regard, the calcium levels are depicted in a saw-toothed pattern in a graph. When the cell membrane bubbles and is damaged, the calcium influx is reduced, with the cell contents being expelled. As a result, the intracellular calcium level becomes lower than the original level.

EXAMPLE 5: INTRACELLULAR MIGRATION OF PEPTIDE eMTDΔ4 (SEQ ID NO: 2) TO TARGET

In order to investigate the source that allowed the intracellular calcium influx observed in Example 4, examination was made of the site at which the peptide eMTDΔ4 (SEQ ID NO: 2) acts. In this regard, the fluorescent tracer fluorescein was labeled to the C-terminal of the peptide eMTDΔ4 (SEQ ID NO: 2) (eMTDΔ4 (SEQ ID NO: 2)-FAM). Then, HeLa cells grown on Lab-Tek chamber glass were incubated with eMTDΔ4 (SEQ ID NO: 2)-FAM for 5 and 10 min before fixation with 1% paraformaldehyde.

Mitochondria were visualized using an antibody to TOM20, which localizes to the outer membrane of the mitochondrion because MTD (SEQ ID NO: 3) is known to migrate to mitochondria, while nuclei were visualized using DAPI. Confocal micrographic images are shown in FIG. 5.

Figure 5:
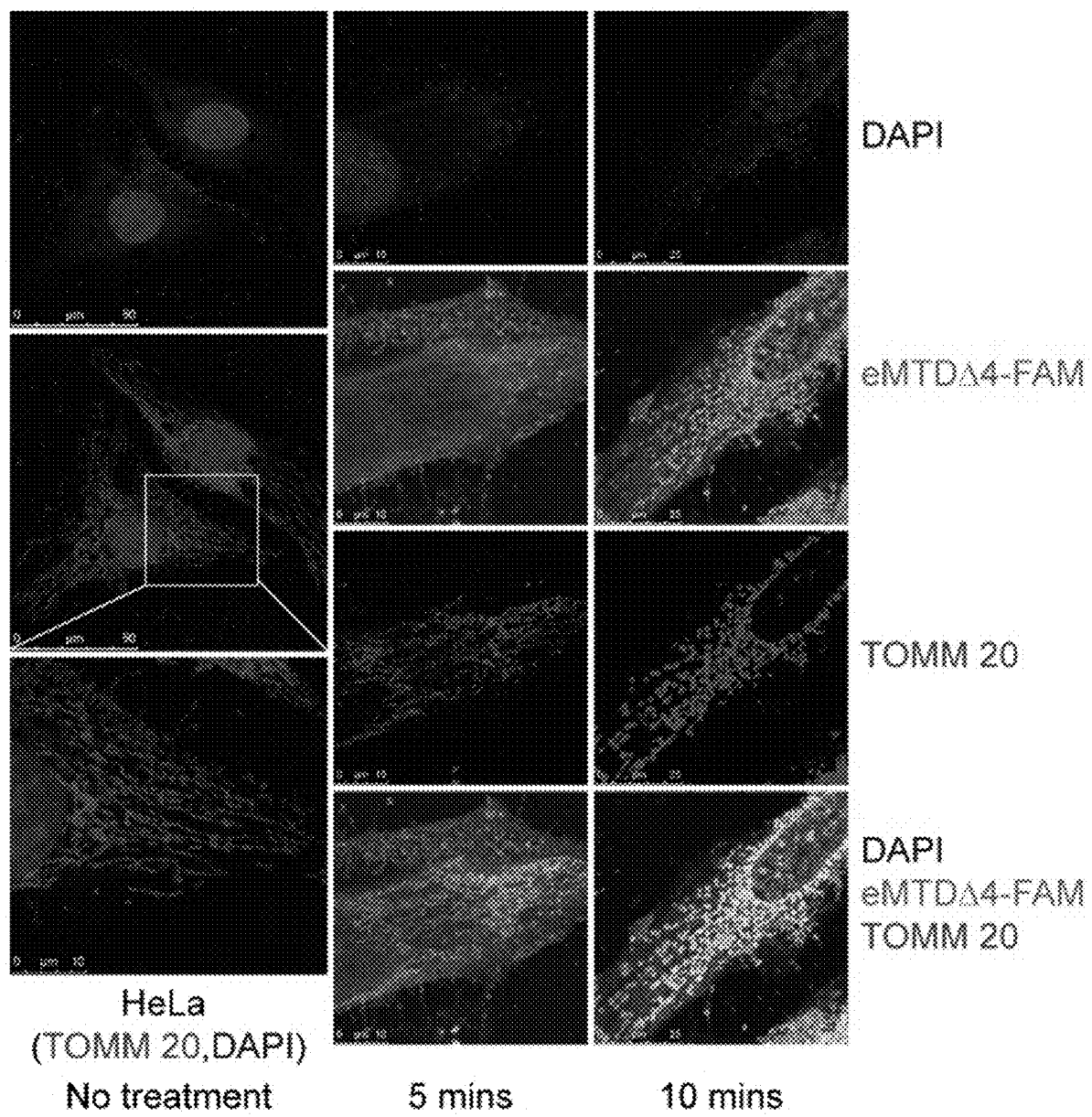
FIG. 5 shows confocal microscopic images of HeLa cells fixed 5 and 10 min after treatment with the peptide eMTDΔ4 (SEQ ID NO: 2) conjugated with a fluorescent (Fluorescein; FAM) according to an embodiment of the present disclosure.

As indicated by the images of FIG. 5, the localization of eMTDΔ4 (SEQ ID NO: 2)-FAM is consistent with the visualized positions of mitochondria. In addition, after treatment with eMTDΔ4 (SEQ ID NO: 2)-FAM, mitochondrial fragmentation was observed morphologically.

EXAMPLE 6: OBSERVATION OF eMTDΔ4 (SEQ ID NO: 2) ACTIVITY IN MITOCHONDRION 6-1. Mitochondrial Swelling In Example 5, eMTDΔ4 (SEQ ID NO: 2)-FAM was observed to localize to mitochondria and to induce mitochondrial fragmentation. Accordingly, examination was further made to see how eMTDΔ4 (SEQ ID NO: 2) practically works at mitochondria in greater detail.

First, livers excised from 6-week-old BalB/C mice were immersed in buffer (250 mM mannitol, 70 mM EGTA, 5 mM HEPES, pH 7.4, 0.1 mM PMSF and 4 rotenone) and completely homogenized using a Teflon Potter-Elvehjem grinder (Sigma). The ground liver was centrifuged at 1000×g for 10 min at 4° C. and the supernatants were centrifuged at 10,000×g for 10 min at 4° C. The pellets thus obtained were suspended in a regeneration buffer (250 mM sucrose, 10 mM HEPES, pH 7.4, 5 mM sodium succinate, 2 mM potassium phosphate, 0.1 mM PMSF, 25 μM EGTA, and 4 rotenone).

The mitochondria thus obtained were treated with 25 μM of eMTD (SEQ ID NO: 1) or eMTDΔ4 (SEQ ID NO: 2), followed by reading absorbance at 540 nm to determine mitochondrial swelling. The results are given in FIG. 6A and Table 5, below. For a positive control, the mitochondria were treated with 200 μM of $Ca^{2+}$ while co-treatment with 200 μM of $Ca^{2+}$ and 20 μM of CsA was conducted for a negative control.

For direct identification, the mitochondria were treated with eMTDΔ4 (SEQ ID NO: 2) (25 μM), $Ca^{2+}$ (200 μM), or $Ca^{2+}$ (200 μM)+CsA (20 μM) and then observed by transmission electron microscopy. The results are given in FIG. 6B.

TABLE 5

| Minute | 0 | 10 | 20 | 30 | 40 | 50 | 60 |
|---|---|---|---|---|---|---|---|
| None | 100% | 98% | 97% | 95% | 95% | 95% | 95% |
| cNoxa del4 | 100% | 79% | 74% | 70% | 68% | 66% | 65% |
| cNoxa | 100% | 86% | 78% | 71% | 68% | 68% | 67% |
| Ca | 100% | 77% | 75% | 73% | 72% | 70% | 70% |
| CsA | 100% | 98% | 98% | 97% | 97% | 96% | 96% |
| Ca + CsA | 100% | 98% | 97% | 96% | 95% | 94% | 93% |
| None | 0% | 0% | 0% | 0% | 0% | 0% | 0% |
| cNoxa del4 | 0% | 0% | 0% | 0% | 0.22% | 0% | 0% |
| cNoxa | 0% | 4% | 4% | 6% | 5% | 5% | 5% |
| Ca | 0% | 0% | 1% | 1% | 1% | 1% | 0% |
| CsA | 0% | 0% | 0% | 0% | 0% | 0% | 0% |
| Ca + CsA | 0% | 0% | 0% | 0% | 0% | 0% | 0% |

Figure 6A:
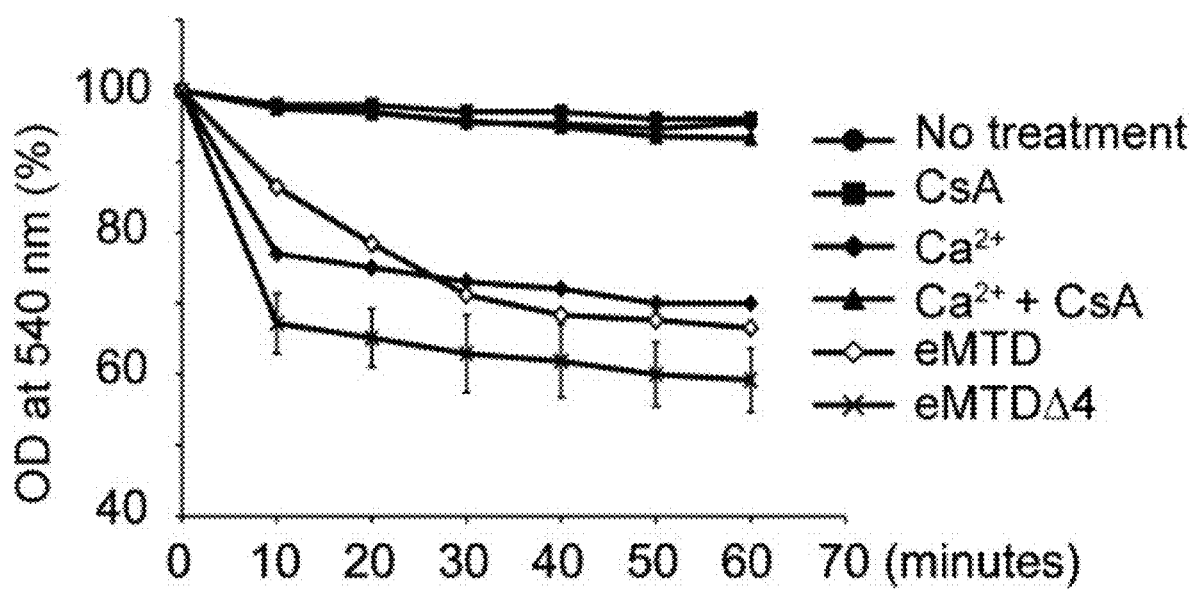
FIG. 6a shows mitochondrial swelling as analyzed by absorbance read at 540 nm after treatment of mitochondria isolated from livers of BalB/C mice with the peptide eMTDΔ4 (SEQ ID NO: 2) according to an embodiment of the present disclosure.
Figure 6B:
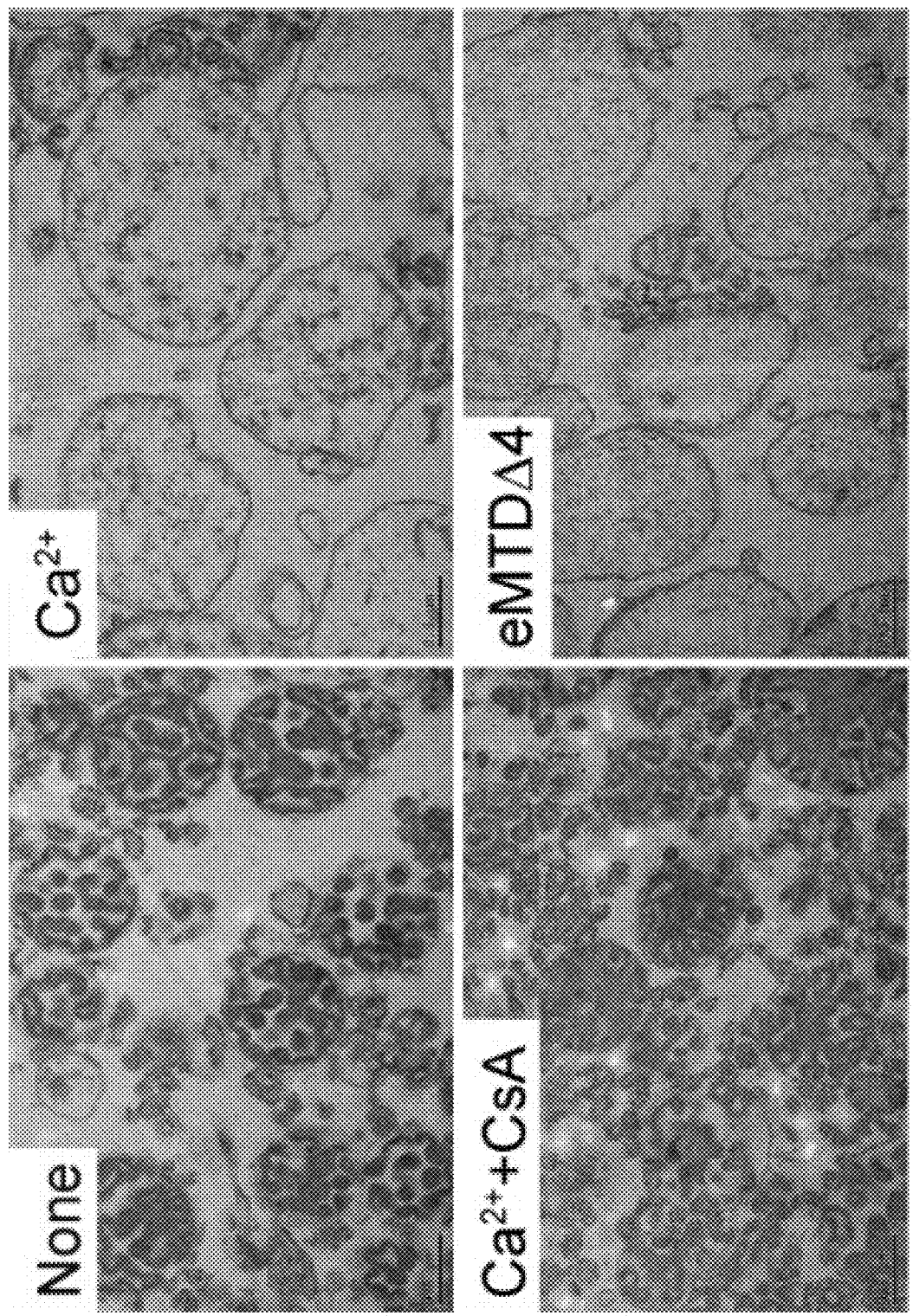
FIG. 6b shows mitochondrial swelling as observed by TEM (transmission electron microscopy) after treatment of mitochondria isolated from livers of BalB/C mice with the peptide eMTDΔ4 (SEQ ID NO: 2) according to an embodiment of the present disclosure.

As indicated by the data of FIGS. 6A and 6B and Table 5, eMTDΔ4 (SEQ ID NO: 2) was observed to induce mitochondrial swelling.

6-2. Mitochondrial PTP

Mitochondria are known to open permeability transition pores (PTP) to allow cytosolic calcium influx. The observation that eMTDΔ4 (SEQ ID NO: 2) migrates to mitochondria and induces cytosolic calcium influx led to investigating the association of the action of eMTDΔ4 (SEQ ID NO: 2) with PTP. To this end, PTP opening was monitored using calcein AM and cobalt ions.

In brief, HeLa cells were grown on a Lab-Tek chamber glass slide one day before the experiment. Immediately before the experiment, the cells were stained with 1 μM of calcein AM and 2 mM of cobalt ions for 20 min and then with 0.1 μM of MitoTracker Red for 2 min. Time-lapse confocal images were taken and are given in FIGS. 7A and 7B. When PTP is opened, mitochondrial calcein AM meets cobalt ions so that the fluorescence of calcein AM is quenched.

Figure 7A:
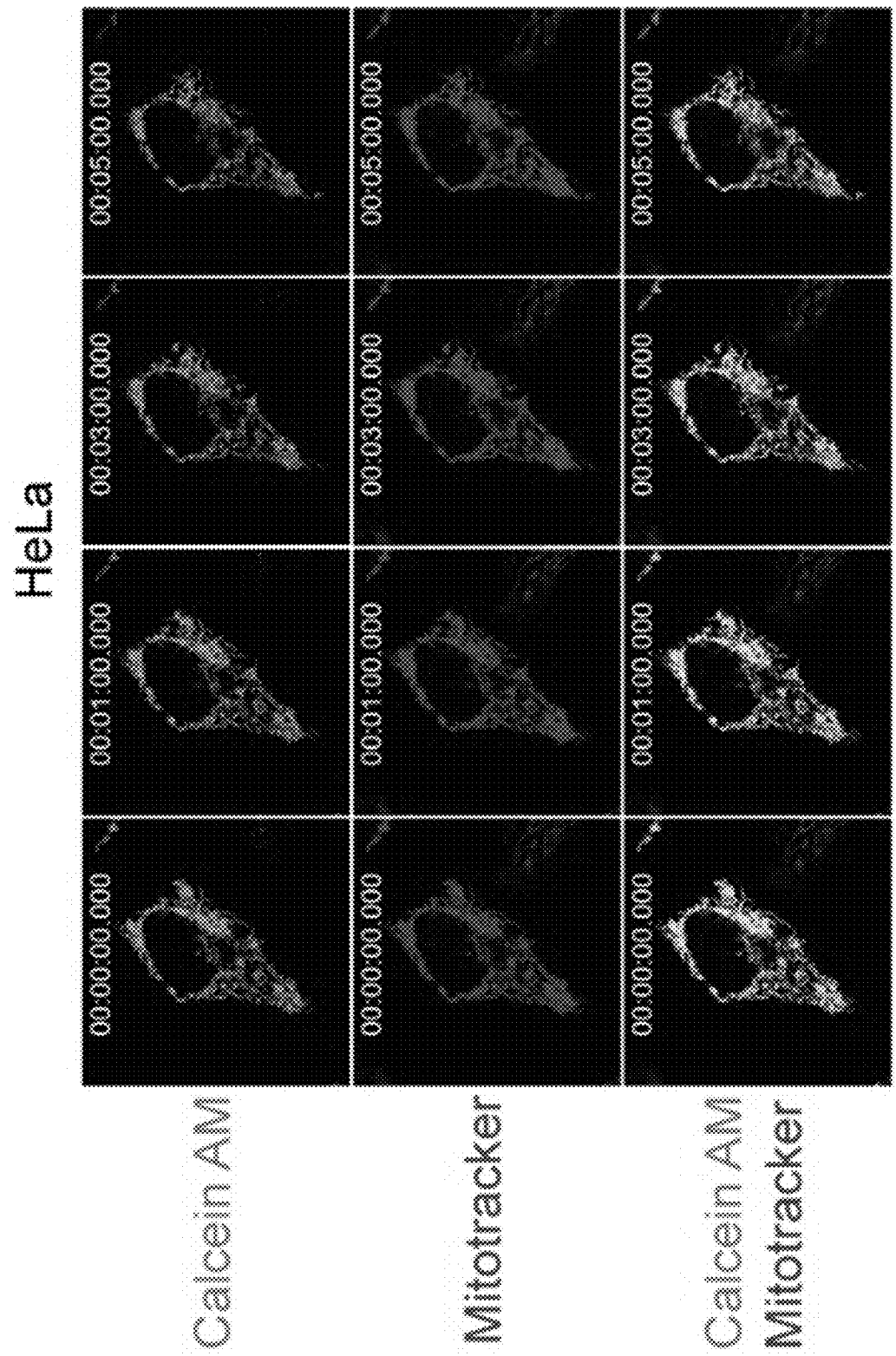
FIG. 7a shows time-lapse, confocal microscopic images of HeLa cells to identify mitochondrial PTP opening after only mitochondria are stained with calcein AM and cobalt ions without treatment with the peptide eMTDΔ4 (SEQ ID NO: 2) according to an embodiment of the present disclosure.
Figure 7B:
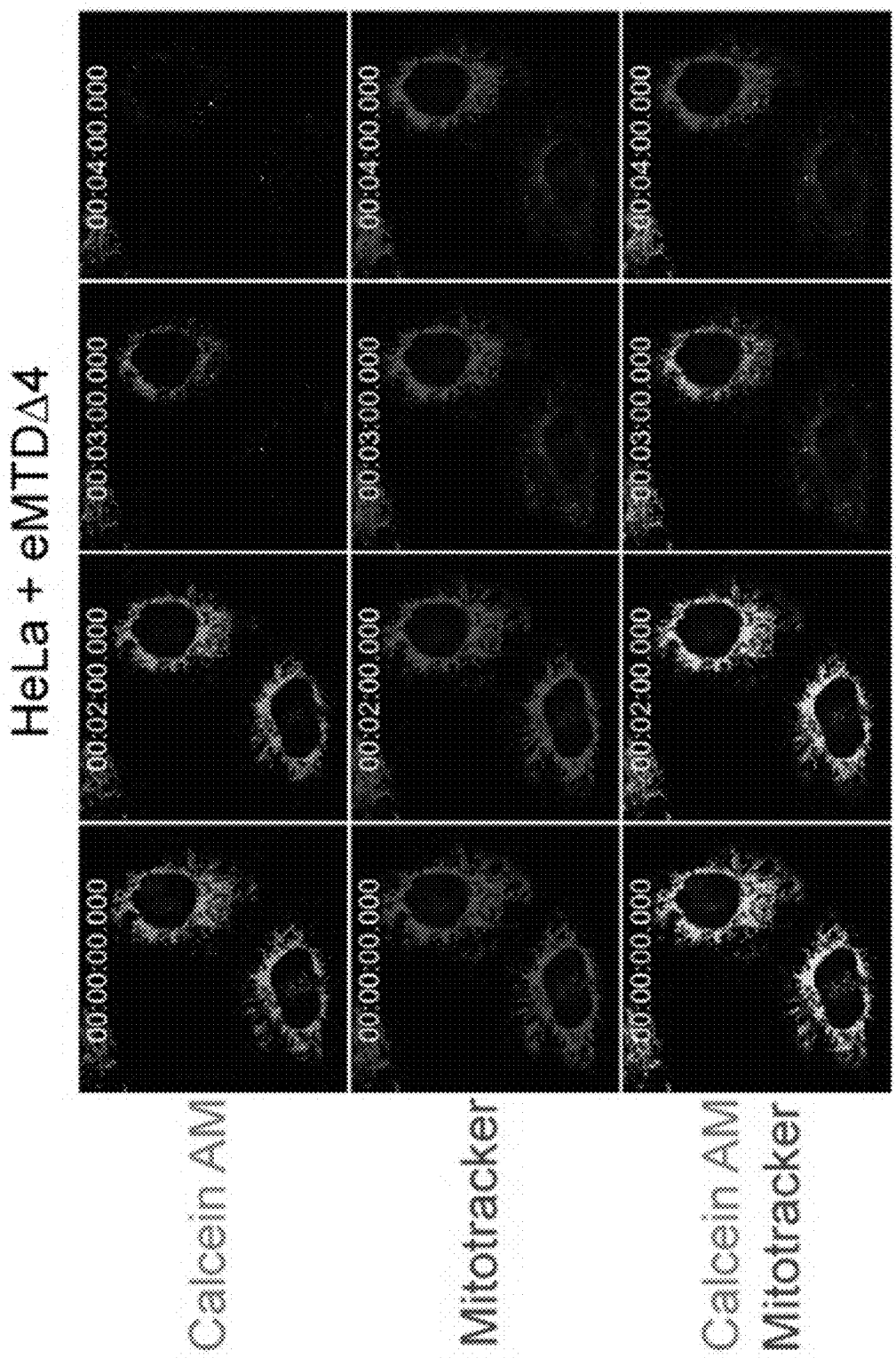
FIG. 7b shows time-lapse, confocal microscopic images of HeLa cells to identify mitochondrial PTP opening after only mitochondria are stained with calcein AM and cobalt ions and the cells are treated with the peptide eMTDΔ4 (SEQ ID NO: 2) according to an embodiment of the present disclosure.

As is understood from the images of FIGS. 7A and 7B, the fluorescence of mitochondrial calcein AM was quenched upon treatment with eMTDΔ4 (SEQ ID NO: 2), implying that the eMTDΔ4 (SEQ ID NO: 2)-induced cytosolic calcium influx is conducted by PTP opening.

EXAMPLE 7: PEPTIDE eMTDΔ4 (SEQ ID NO: 2)-INDUCED CELL DEATH AND ROS GENERATION

In addition to an increase in intracellular calcium level, reactive oxygen species (ROS) generation is an important factor for cell death. Examination was made of the role of ROS in the process of eMTDΔ4 (SEQ ID NO: 2)-induced cell death.

In brief, HeLa cells were grown to 70% confluency on a Lab-Tek chamber glass slide one day before the experiment. The cells were stained for 10 min with 5 μM of the mitochondrial ROS indicator MitoSox (Invitrogen) in order to visualize ROS generation. Then, the cells were incubated with eMTDΔ4 (SEQ ID NO: 2) for 10 min during which confocal micrographic images were taken to monitor cell morphologies and ROS generation. The results are given in FIGS. 8A to 8C.

Figure 8A:
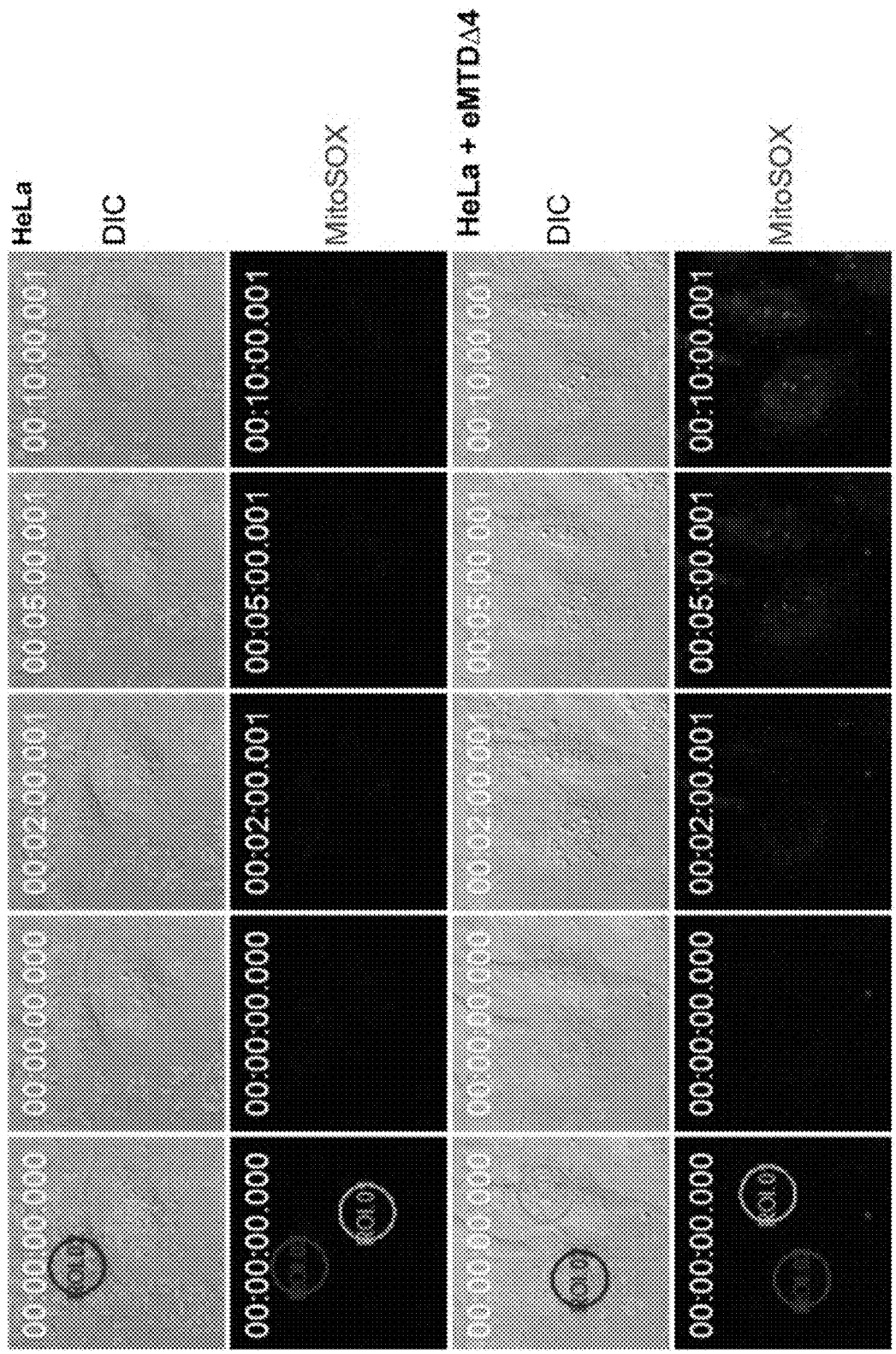
FIG. 8a shows time-lapse, confocal microscopic images of HeLa cells after the cells are stained with the mitochondrial reactive oxygen species indicator MitoSox and then treated with or without 20 of the peptide eMTDΔ4 (SEQ ID NO: 2) according to an embodiment of the present disclosure.
Figure 8B:
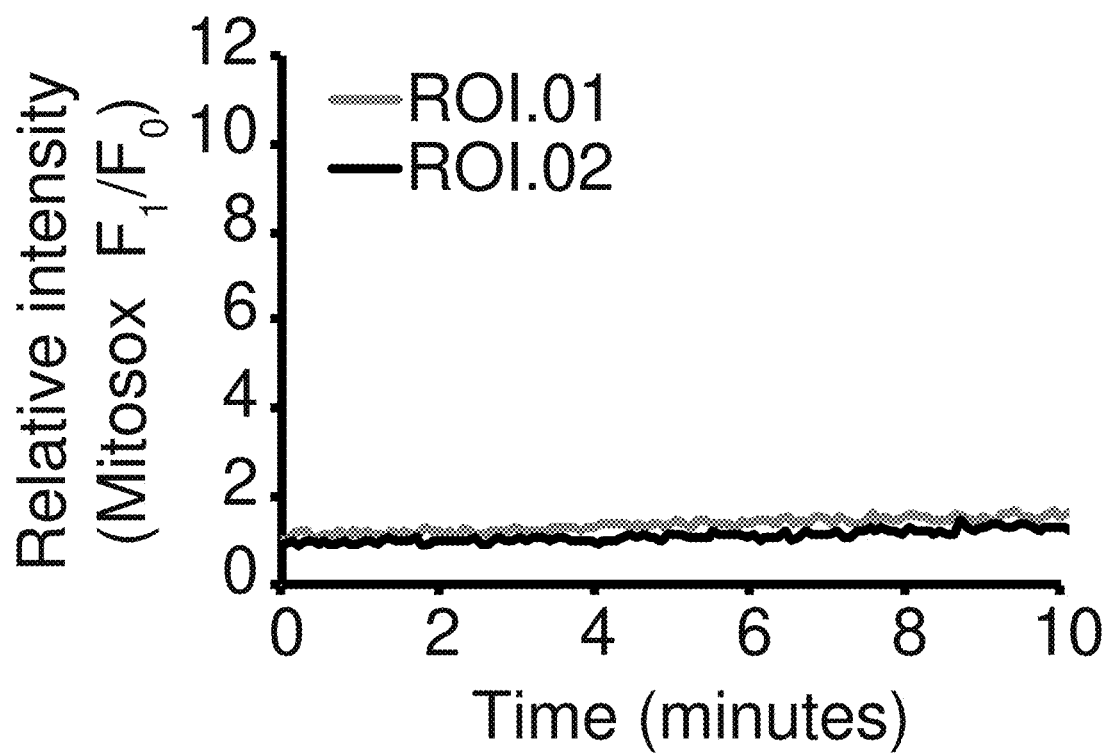
FIG. 8b is a graph showing MitoSox intensities within ROI (region of interest) of time-lapse confocal microscopic images of HeLa cells stained with the mitochondrial reactive oxygen species indicator MitoSox without eMTDΔ4 (SEQ ID NO: 2) treatment according to an embodiment of the present disclosure.
Figure 8C:
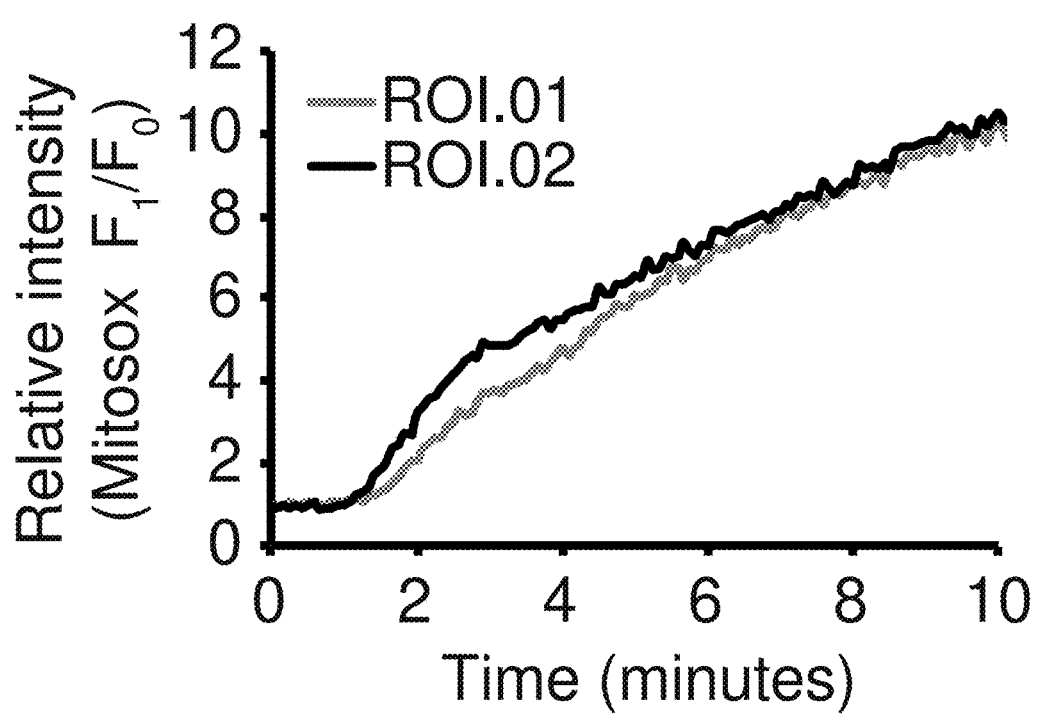
FIG. 8c is a graph showing MitoSox intensities within ROI (region of interest) of time-lapse confocal microscopic images of HeLa cells stained with the mitochondrial reactive oxygen species indicator MitoSox and then treated with 20

As shown in FIGS. 8A to 8C, the non-treated HeLa cells scarcely changed in cell morphology and ROS level whereas eMTDΔ4 (SEQ ID NO: 2)-treated HeLa cells abruptly increased in ROS level just after the cell membrane bubbling. Although not demonstrating that ROS generated in mitochondria is a direct cause of cell death, this result indicates that the peptide eMTDΔ4 (SEQ ID NO: 2) of the present disclosure causes ROS generation in mitochondria in the light of the ROS generation just after the bubbling (cell membrane damage).

EXAMPLE 8: PEPTIDE eMTDΔ4 (SEQ ID NO: 2)-INDUCED CELL MEMBRANE DAMAGE

8-1. Confocal Microscopy

In order to investigate the temporal order and cause relation between the introduction of eMTDΔ4 (SEQ ID NO: 2) and the damage of mitochondrial membrane and cell membrane, mitochondria were visualized by transfecting Mito-DsRed2 into HeLa cells one day before the experiment. Thereafter, eMTDΔ4 (SEQ ID NO: 2)-FAM was applied to the HeLa cells images of which were then taken every five seconds for 10 min under a confocal microscope. The results are given in FIG. 9.

As shown in FIG. 9, eMTDΔ4 (SEQ ID NO: 2)-FAM diffused into the cytosol through the cell membrane bubbles from the time when the bubbles were formed and after eMTDΔ4 (SEQ ID NO: 2) reached thereto, the mitochondria started to undergo fragmentation.

These data imply that eMTDΔ4 (SEQ ID NO: 2) is more likely to diffuse into the cytosol after cell membrane damage than to be introduced through channels or other receptors. The eMTDΔ4 (SEQ ID NO: 2) introduced by diffusion is considered to localize to mitochondria to introduce cell death.

8-2. Two-Step Assay

The mechanism in which eMTDΔ4 (SEQ ID NO: 2) directly damages cell membranes was examined using a two-step assay.

In brief, DOPS, DOPE, and DOPC (Avanti Polar Lipids) were dissolved at the ratio of 2:4:3 in chloroform, followed by vaporization. The residue was again dissolved at the concentration of 2 mg/mL in $TbCl_3$ buffer (15 mM $TbCl_3$, 50 mM sodium citrate, 20 mM HEPES, 150 mM NaCl, pH 7.4). The lipid mixture was extruded by Mini extruder (Avanti Polar Lipids) with a 400 nm to prepare liposomes which were washed with washing buffer (150 mM NaCl, 20 mM HEPES, pH 7.4) and then resuspended in an assay buffer (50 DPA, 150 M NaCl, 20 mM HEPES, pH 7.4). The suspension was plated into 96-well plates and treated with 0, 10, or 25 μM of eMTD (SEQ ID NO: 1) or eMTDΔ4 (SEQ ID NO: 2). After stimulation with 276 nm laser, fluorescence was read at 490 nm. The results are given in FIGS. 10A to 10C and Table 6.

TABLE 6

|  |  | eMTD (SEQ ID NO: 1) | eMTD Δ4 (SEQ ID NO: 2) |
|---|---|---|---|
| 0 μM | Relative Fluorescence Intensity | 0% | 0% |
|  | Standard Deviation | 0% | 0% |
| 10 μM | Relative Fluorescence Intensity | 27% | 25% |
|  | Standard Deviation | 1% | 1% |
| 25 μM | Relative Fluorescence Intensity | 55% | 51% |
|  | Standard Deviation | 3% | 1% |

As is understood from data of FIGS. 10A to 10C and Table 6, higher fluorescence intensity was detected upon treatment with eMTD (SEQ ID NO: 1) or eMTDΔ4 (SEQ ID NO: 2), indicating that $TbCl_3$ was released through damaged portions of lipid membranes of the liposomes. Accordingly, it is concluded that eMTD (SEQ ID NO: 1) and eMTDΔ4 (SEQ ID NO: 2) directly act on cell membrane to damage the lipid structure of the cell membrane.

This result was directly observed. In this regard, MDA-MB-231 cells were treated with eMTDΔ4 (SEQ ID NO: 2) and pores formed on the cell membrane were observed using an atomic force microscope. Measurements were statistically treated according time and the data thus obtained are given in FIG. 10D and Table 7.

TABLE 7

| Length | Counts t = 30 sec | Counts t = 2 min | Counts t = 5 min | Counts t = 40 min |
|---|---|---|---|---|
| >0.625 | 1.408451 | 0 | 0 | 0 |
| 0.675~0.975 | 38.02817 | 20.63492 | 14.81481 | 2.5 |
| 1.025~1.325 | 43.66197 | 38.09524 | 39.50617 | 22.5 |
| 1.375~1.675 | 9.859155 | 20.63492 | 20.98765 | 22.5 |
| 1.725~2.025 | 4.225352 | 14.28571 | 13.58025 | 22.5 |
| 2.075~2.725 | 2.816901 | 6.349206 | 9.876543 | 22.5 |
| 2.775< | 0 | 0 | 1.234568 | 7.5 |
| S.D | 18.47933 | 13.65448 | 13.38917 | 10.47957 |

As can be seen in FIG. 10d and Table 7, larger pores were formed with time after treatment of MDA-MB-231 cells with eMTDΔ4 (SEQ ID NO: 2), demonstrating that eMTDΔ4 (SEQ ID NO: 2) gave damage to the surface of the MDA-MB-231 cell membrane.

As described hitherto, the present disclosure pertains to a cell death-inducing peptide that rapidly acts and, more particularly, to a peptide, derived from Noxa protein (SEQ ID NO: 4), consisting of 16 amino acid residues including MTD (SEQ ID NO: 3). The peptide is designated extended MTD (eMTD; (SEQ ID NO: 1)) because it contains the 10-mer MTD. eMTD (SEQ ID NO: 1) rapidly exhibits potent necrotic cell death in various cell lines and, as such, can be applied to the treatment of various diseases including cancer when used in conjugation with peptides or materials for targeting specific cells.

What is claimed is:

1. A peptide comprising a sequence consisting of the amino acid sequence of SEQ ID NO: 1 or 2, wherein optionally the peptide further comprises a tumor-homing peptide (THP) conjugated to the N- or C-terminus of the peptide and the THP comprises an amino acid sequence selected from the group consisting of SEQ ID NOs: 5 to 31.

2. The peptide of claim 1, wherein the peptide comprises said THP conjugated to the N- or C-terminus of the peptide.

3. A composition comprising the peptide of claim 1 or 2.

4. The peptide of claim 1, wherein the peptide comprises a sequence consisting of SEQ ID NO: 1, wherein optionally the peptide further comprises a tumor-homing peptide (THP) conjugated to the N- or C-terminus of the peptide and the THP comprises an amino acid sequence selected from the group consisting of SEQ ID NOs: 5 to 31.

5. The peptide of claim 4, wherein the peptide comprises said THP further comprises a THP conjugated to the N- or C-terminus of the peptide.

6. The peptide of claim 1, wherein the peptide comprises a sequence consisting of SEQ ID NO: 2, wherein optionally the peptide further comprises a tumor-homing peptide (THP) conjugated to the N- or C-terminus of the peptide and the THP comprises an amino acid sequence selected from the group consisting of SEQ ID NOs: 5 to 31.

7. The peptide of claim 6, wherein the peptide comprises said THP further comprises a THP conjugated to the N- or C-terminus of the peptide.

8. The peptide of claim 1, wherein the amino acid sequence of the peptide consists of the amino acid sequence of SEQ ID NO: 1.

9. The peptide of claim 1, wherein the amino acid sequence of the peptide consists of: (a) the amino acid sequence of SEQ ID NO: 1 and (ii) the amino acid sequence of a THP of an amino acid sequence selected from SEQ ID NOs: 5 to 31.

10. The peptide of claim 1, wherein the amino acid sequence of the peptide consists of the amino acid sequence of SEQ ID NO: 2.

11. The peptide of claim 1, wherein the amino acid sequence of the peptide consists of: (a) the amino acid sequence of SEQ ID NO: 2 and (ii) the amino acid sequence of a THP of an amino acid sequence selected from SEQ ID NOs: 5 to 31.

12. A polynucleotide coding for the peptide of claim 1 or 2.

13. A recombinant vector carrying the polynucleotide of claim 12.

14. A transformed cell transformed with the recombinant vector of claim 13.

15. A method for the Method for prevention or treatment of cancer comprising: administering to a subject a composition comprising the peptide of claim 1 or 2.

16. The method of claim 15, wherein the cancer is lung cancer, breast cancer, liver cancer, melanoma, stomach cancer, pancreatic cancer, colorectal cancer, ovarian cancer, renal cell carcinoma, prostate cancer, or brain tumor.

* * * * *